(12) United States Patent
Loutherback et al.

(10) Patent No.: US 8,783,467 B2
(45) Date of Patent: *Jul. 22, 2014

(54) BUMP ARRAY DEVICE HAVING ASYMMETRIC GAPS FOR SEGREGATION OF PARTICLES

(71) Applicant: The Trustees of Princeton University, Princeton, NJ (US)

(72) Inventors: Kevin Loutherback, Berkeley, CA (US); James C. Sturm, Princeton, NJ (US); Robert Austin, Princeton, NJ (US); Keith Morton, Boucherville (CA); Jason Puchalla, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/708,425

(22) Filed: Dec. 7, 2012

(65) Prior Publication Data
US 2013/0098813 A1    Apr. 25, 2013

Related U.S. Application Data

(63) Continuation of application No. 12/509,175, filed on Jul. 27, 2009, now Pat. No. 8,579,117.

(60) Provisional application No. 61/135,854, filed on Jul. 24, 2008.

(51) Int. Cl.
*B03B 5/00* (2006.01)

(52) U.S. Cl.
USPC ............................ 209/210; 209/143; 209/208

(58) Field of Classification Search
USPC .......... 209/134, 136, 138, 142, 143, 208, 210
See application file for complete search history.

(56) References Cited

U.S. PATENT DOCUMENTS

| 5,427,663 A | 6/1995 | Austin et al. |
| 5,707,799 A | 1/1998 | Hansmann et al. |

(Continued)

FOREIGN PATENT DOCUMENTS

| WO | 9808931 A1 | 3/1998 |
| WO | 03001193 A1 | 1/2003 |

(Continued)

OTHER PUBLICATIONS

Davis, et al., "Deterministic hydrodynamics: Taking blood apart," PNAS, (Oct. 3, 2006), vol. 103, No. 40, 14779-14784.

(Continued)

*Primary Examiner* — Joseph C Rodriguez
(74) *Attorney, Agent, or Firm* — Kilpatrick Townsend & Stockton LLP

(57) ABSTRACT

The disclosure relates to obstacle array devices (also known as bump array devices) for separating populations of particles by size. Improvements over previous obstacle array devices are realized by causing the fluid velocity profile across gaps between obstacles to be asymmetrical with respect to the plane that bisects the gap and is parallel to the direction of bulk fluid flow. Such asymmetry can be achieved by selecting the shape(s) of the obstacles bounding the gap such that the portions of the obstacles upstream from, downstream from or bridging the narrowest portion of the gap are asymmetrical with respect to that plane.

Improvements are also realized by using obstacles that have sharp edges bounding the gaps. Other improvements are realized by selecting obstacle shapes such that the critical particle dimensions defined by the gaps in two different fluid flow directions differ.

20 Claims, 16 Drawing Sheets

(56) References Cited

U.S. PATENT DOCUMENTS

| | | | |
|---|---|---|---|
| 5,715,946 | A | 2/1998 | Reichenbach |
| 5,837,115 | A | 11/1998 | Austin et al. |
| 5,885,470 | A | 3/1999 | Parce et al. |
| 6,632,652 | B1 | 10/2003 | Austin et al. |
| 6,762,059 | B2 | 7/2004 | Chan et al. |
| 6,881,317 | B2 | 4/2005 | Huang et al. |
| 7,150,812 | B2 | 12/2006 | Huang et al. |
| 8,425,254 | B2 | 9/2009 | Huang et al. |
| 7,735,652 | B2 | 6/2010 | Inglis et al. |
| 7,988,840 | B2 | 8/2011 | Huang et al. |
| 8,168,389 | B2 | 5/2012 | Shoemaker et al. |
| 8,282,799 | B2 | 10/2012 | Huang et al. |
| 8,304,230 | B2 | 11/2012 | Toner et al. |
| 8,579,117 | B2 * | 11/2013 | Loutherback et al. ........ 209/210 |
| 2008/0124779 | A1 | 5/2008 | Oh et al. |
| 2008/0135502 | A1 | 6/2008 | Pyo et al. |
| 2010/0006479 | A1 | 1/2010 | Reichenbach |
| 2010/0301171 | A1 | 12/2010 | Wood |
| 2012/0037544 | A1 | 2/2012 | Lane et al. |

FOREIGN PATENT DOCUMENTS

| | | | |
|---|---|---|---|
| WO | 2004037374 | A2 | 5/2004 |
| WO | 2006031095 | A1 | 3/2006 |
| WO | 2007130682 | | 11/2007 |
| WO | 2007130682 | A2 | 11/2007 |
| WO | 2009106873 | A2 | 9/2009 |

OTHER PUBLICATIONS

Galajda et al., "A Wall of Funnels Concentrates Swimming Bacteria," Journal of Bacteriology, (Dec. 2007) vol. 189, No. 23, 8704-8707.

Galajda, et al., "Funnel ratchets in biology at low Reynolds number: choanotaxis," Journal of Modern Optics, vol. 55, Nos. 19-20, 10-20, (Nov. 2008) 3413-3422.

Inglis et al., "Critical particle size for fractionation by deterministic lateral displacement," Lab Chip (2006) 6, 655-658.

Keller et al., "Separation quality of a geometric ratchet," The American Physical Society, Physical Review Letters, Dec. 31, 2002, 041927.

Loutherback et al., "Deterministic Microfluidic Ratchet," The American Physical Society, Physical Review Letters, Jan. 30, 2009, 045301-1-045301-4.

Search Report, European Patent Application No. 09801077.0-2204/ 2304414, dated Sep. 20, 2012.

Ashcroft, N., et al., "Solid State Physics," Saunders College Publishing, Fort Worth, only Table of Contents and List of Important Tables, 1976.

Becker, W., et al., "Fabrication of microstructures with height aspect ratios and great structural heights by synchrotron radiation lithography, galvanoforming, and plastic moulding (L 1 GA process)," Microelectronic Engineering, 4(1 ), May 1986, pp. 35-36.

Becker, H., et al., "Planar Quartz Chips with Submicron Channels for Two-Dimensional Capillary Electrophoresis Applications," J. Micromech. Microeng., 8(1),Mar. 1998, pp. 24-28.

Berg, H., "Random Walks in Biology," Princeton University Press, New Jersey, 1993, p. 56, Table of Contents and pp. 51-58.

Chou, C., et al. "Sorting by Diffusion: An Asymmetric Obstacle Course for Continuous Molecular Separation," Proceedings of the National Academy of Sciences, vol. 96, Nov. 23, 1999, 4 pages.

Duke, T., et al. "Microfabricated Sieve for the Continuous Sorting of Macromolecurles," Physical Review Letters, vol. 80, Feb. 16, 1998. 4 pages.

Ertas, D. "Lateral Separation of Macromolecules and Polyeletrolytes in Microlithographic Arrays," Harvard University, Feb. 1, 2008, 4 pages.

Giddings, J., "Unified Separation Science," Wiley, New York, 1991, Table of Contents and pp. xi-xv.

Giddings, J., "Eddy's diffusion in chromatography," Nature, Aug. 1, 1959, pp. 357-358.

Giddings, J., "Field-flow fractionation: Analysis of macromolecular, colloidal, and particulate materials," Science, Jun. 4, 1993, pp. 1456-1465.

Han, J., et al. "Separation of Long DNA Molecules in a Microfabricated Entropic Trap Array," Science, vol. 288, May 12, 2000, 4 pages.

Huang, L., et al., "A DNA prism for high-speed continuous fractionation of large DNA molecules," Nat. Biotech no!. 20(1 0), Oct. 2002, pp. 1048-1051.

Huang, L., et al. "Role of Molecular Size in Ratchet Fractionation," Physical Review Letters, vol. 89, Oct. 21, 2002, 4 pages.

Turner, S., et al. "Confinement-Induced Entropic Reciol of Single DNA Molecules in a Nanofluidic Structure," Physical Review Letters, vol. 88, Mar. 25, 2002, 4 pages.

US 7,425,254, 09/2008, Huang et al. (withdrawn)

* cited by examiner

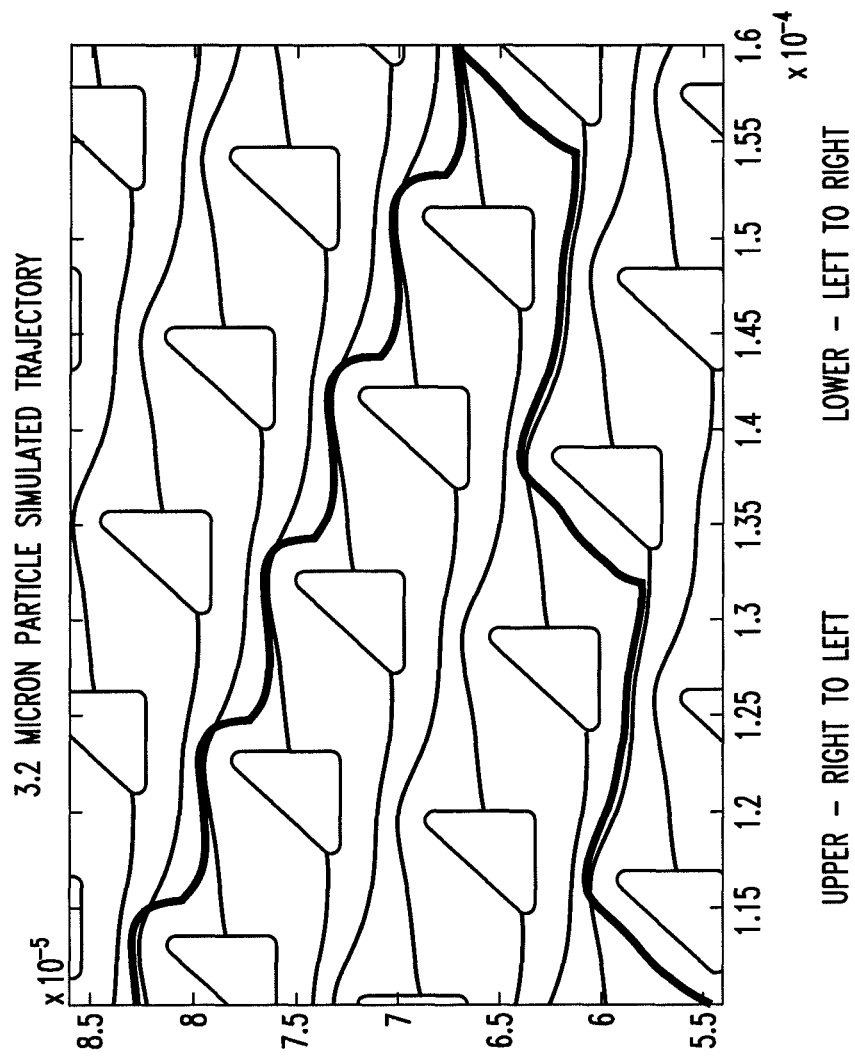

NORMALIZED VELOCITY

COMPARISON OF CRITICAL PARTICLE SIZES
BETWEEN CIRCULAR POSTS AND TRIANGULAR POSTS

BUMP ARRAY DEVICE HAVING ASYMMETRIC GAPS FOR SEGREGATION OF PARTICLES

CROSS-REFERENCES TO RELATED APPLICATIONS

This application is a continuation of U.S. patent application Ser. No. 12/509,175, filed Jul. 24, 2009, which claims the benefit of U.S. Provisional Application Ser. No. 61/135,854, filed Jul. 24, 2008, which are incorporated herein by reference as if fully set forth.

STATEMENT REGARDING FEDERALLY SPONSORED RESEARCH OR DEVELOPMENT

This work was supported in part by a grant from DARPA (Grant No. W911NF-07-1-0082), U.S. Air Force Office of Scientific Research (Grant No. FA9550-05-01-03), National Science Foundation Cornell Nanobiology Technology Center (Grant No. BSC-ECS9876771) and an STTR contract (National Institutes of Health contract no. 5R41CA128782-02) and the U.S. Government may have certain rights in this invention.

BACKGROUND OF THE DISCLOSURE

The disclosure relates generally to the field of separation of particles such as spheres, cells, viruses, and molecules. In particular, the disclosure relates to separation of particles based on their flow behavior in a fluid-filled field of obstacles in which advective transport of particles by a moving fluid overwhelms the effects of diffusive particle transport.

Separation of particles by size or mass is a fundamental analytical and preparative technique in biology, medicine, chemistry, and industry. Conventional methods include gel electrophoresis, field-flow fractionation, sedimentation and size exclusion chromatography. More recently, separation of particles and charged biopolymers has been described using arrays of obstacles through particles pass under the influence of fluid flow or an applied electrical field. Separation of particles by these obstacle-array devices is mediated by interactions among the biopolymers and the obstacles and by the flow behavior of fluid passing between the obstacles.

A variety of microfabricated sieving matrices have been disclosed for separating particles (Chou et. al., 1999, Proc. Natl. Acad. Sci. 96:13762; Han, et al., 2000, Science 288:1026; Huang et al., 2002, Nat. Biotechnol. 20:1048; Turner et al., 2002, Phys. Rev. Lett. 88(12):128103; Huang et al., 2002, Phys. Rev. Lett. 89:178301; U.S. Pat. No. 5,427,663; U.S. Pat. No. 7,150,812; U.S. Pat. No. 6,881,317). These matrices depend on accurate fabrication of small features (e.g., posts in a microfluidic channel). The accuracy with which small features can be fabricated is limited in all microfabrication methods, especially as feature size decreases. The strength and rigidity of materials in which small features of fabricated can also limit the practical usefulness of the fabricated device. Furthermore, the small size of the gaps between obstacles in such matrices can render the matrices susceptible to clogging by particles too large to fit between the obstacles. Micrometer- and nanometer-scale manufacturing also require state-of-the-art fabrication techniques, and devices fabricated using such methods can have high cost.

Previous bump array (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a bump array operates essentially by segregating particles passing through an array (generally, a periodically-ordered array) of obstacles, with segregation occurring between particles that follow an "array direction" that is offset from the direction of bulk fluid flow or from the direction of an applied field.

At the level of flow between two adjacent obstacles under conditions of relatively low Reynold's number, fluid flow generally occurs in a laminar fashion. Considering the volumetric flow between two obstacles in hypothetical layers (e.g., modeling the flow by considering multiple adjacent stream tubes of equal volumetric flow between the obstacles, as shown in FIG. 8 of U.S. Pat. No. 7,150,812), the likelihood that fluid in a layer will pass on one side or the other of the next (i.e., downstream) obstacle is calculable by standard methods (see, e.g., Inglis et al., 2006, Lab Chip 6:655-658). For an ordered array of obstacles offset from the direction of bulk fluid flow, the arrangement of the obstacles will define an array direction corresponding to the direction in which the majority of fluid layers between two obstacles travels. A minority of fluid layers will travel around the downstream obstacle in a direction other than the array direction.

The path that a particle passing between the two obstacles will take depends the flow of the fluid in the layers occupied by the particle. Conceptually, for a particle having a size equal to one of the hypothetical fluid layers described in the preceding paragraph, the particle will follow the path of the fluid layer in which it occurs, unless it diffuses to a different layer. For particles larger than a single fluid layer, the particle will take the path corresponding to the majority of the fluid layers acting upon it. Particles having a size greater than twice the sum of the thicknesses of the minority of layers that travel around a downstream obstacle in the direction other than the array direction will necessarily be acted upon by more fluid layers moving in the array direction, meaning that such particles will travel in the array direction. This concept is also illustrated in FIGS. 5-11 of U.S. Pat. No. 7,150,812. Thus, there is a "critical size" for particles passing between two obstacles in such an array, such that particles having a size greater to that critical size will travel in the array direction, rather than in the direction of bulk fluid flow and particles having a size less than the critical size will travel in the direction of bulk fluid flow. Particles having a size precisely equal to the critical size have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

A method of improving the separating ability of obstacle arrays without requiring a decrease in the size of the array features or the accuracy of microfabrication techniques used to make them would be highly beneficial. The present invention relates to such methods and obstacles arrays made using such methods.

BRIEF SUMMARY OF THE DISCLOSURE

The invention relates to bump array devices for segregating particles by size. In one embodiment, these devices include a body that defines a microfluidic flow channel. The channel is shaped and sized so that it is suitable for containing fluid flowing in a first direction (i.e., the direction of bulk fluid flow through the device). Within the channel are disposed an array of obstacles. The obstacles extend across the flow channel (i.e., fluid passing through the channel flows between and among the obstacles, but still in the direction of bulk fluid flow overall. The obstacles are arranged in rows and columns. The rows define an array direction that differs from the first direction by a tilt angle ($\epsilon$) that has a magnitude greater than zero. The obstacles in columns define gaps between themselves through which the fluid can flow generally transversely with respect to the columns (i.e., generally in the direction of bulk fluid flow, but with local directional variations as the fluid flows around and between individual obstacles). The obstacles are shaped such that the surfaces of two obstacles defining a gap are asymmetrically oriented about the plane that extends through the center of the gap and that is parallel to the first direction. In this configuration, the velocity profile of fluid flowing through the gap is asymmetrically oriented about the plane. As a result, the critical particle size for particles passing through the gap adjacent to one of the obstacles is different than the critical particle size for particles passing through the gap adjacent to the other of the obstacles.

The surfaces of the two obstacles can, for example, be non-parallel, substantially planar surfaces. For example, each of the two obstacles can have a triangular cross-section. As an alternative example, the surface of one of the obstacles can be curved and the surface of the other obstacle can be substantially planar. For ease of construction, for example, the flow channel can bounded by a pair of parallel, substantially planar surfaces between which the obstacles extend.

In one embodiment, the columns of obstacles repeat periodically. In a preferred example, the periodicity with which the columns repeat is equal to $1/\epsilon$ when $\epsilon$ is measured in radians.

The devices described herein can be filled with fluid and coupled with one or more fluid handling apparatus for providing liquid to, withdrawing liquid from, or both providing liquid to and withdrawing liquid from the flow channel.

The invention also relates to another kind of bump array devices for segregating particles by size. These devices include a body that defines a microfluidic flow channel for containing fluid flow in a first direction and a second direction. An array of obstacles is disposed within the flow channel and the obstacles extend across the flow channel. The obstacles are arranged in rows and columns, and the rows define an array direction that differs from the first direction by a tilt angle ($\epsilon$) that has a magnitude greater than zero. The obstacles in columns define gaps between themselves through which the fluid can flow in the first direction generally transversely with respect to the columns and through which the fluid can flow in the second direction generally transversely with respect to the column. The obstacles are shaped such that the critical particle size for particles passing through the gap in the first direction is different than the critical particle size for particles passing through the gap in the second direction. The first and second directions can be offset at an angle of from 120 to 180 degrees, for example. In a preferred configuration, the first and second directions are offset by 180 degrees.

The invention also relates to methods of using such devices to segregate particles by size.

BRIEF SUMMARY OF THE SEVERAL VIEWS
OF THE DRAWINGS

FIG. 1 is a schematic diagram of cross-section of a "bump array" device having right triangularly-shaped obstacles disposed in a microfluidic channel. In the figure, fluid flow alternates between the right-to-left and left-to-right directions, as indicated by the double-headed arrow marked, "Fluid Flow." In this array, right triangular posts are disposed in a square lattice arrangement that is tilted with respect to directions of fluid flow. The tilt angle $\epsilon$ (epsilon) is chosen so the device is periodic. In this embodiment, a tilt angle of 18.4 degrees (⅓ radian) makes the device periodic after three rows. The gap between posts is denoted G with triangle side length S and array pitch P. Streamlines are shown extending between the posts, dividing the fluid flow between the posts into three regions ("stream tubes") of equal volumetric flow.

FIG. 2, consisting of FIGS. 2A, 2B, and 2C, shows the trajectories of spherical polystyrene beads of three different sizes in an array of the type shown in FIG. 1 as the direction of fluid flow is cycled back and forth twice. The orientation of the right triangular posts is denoted in the lower right of each figure. Right isosceles triangles are 6 microns on a side with post to post separation of 10 microns and a tilt angle of 5.71 degrees (0.1 radian). Particle sizes are 1.1 microns in FIG. 2A, 3.1 microns in FIG. 2B, and 1.9 microns in FIG. 2C. Particles shown in FIGS. 2A and 2B retrace their paths when the direction of the fluid is switched, with the particles in FIG. 2A generally following the fluid direction in each fluid flow direction and the particles in FIG. 2B generally following the array direction in each fluid flow direction. By contrast, the trajectory of the particles shown in FIG. 2C varies with the direction of the fluid flow. In FIG. 2C, small arrows indicate the direction of the fluid along the particle path; the particles generally follow the fluid direction when the fluid flow direction is left-to-right and generally follow the array direction when the fluid flow direction is right-to-left.

FIG. 3 consists of three diagrams of the simulated trajectories of particles moving through an array of right triangular posts disposed in a microfluidic flow channel in which fluid flow alternates between the right-to-left and left-to-right directions. FIG. 3A shows simulated trajectories of 1.0-micrometer diameter particles. FIG. 3B shows simulated trajectories of 3.6-micrometer diameter particles. FIG. 3C shows simulated trajectories of 3.2-micrometer diameter particles. In these diagrams, the 1.0-micrometer diameter particles are smaller than the critical size of the array in both fluid flow directions, the 3.6-micrometer diameter particles are larger than the critical size of the array in both fluid flow directions, and the 3.2-micrometer diameter particles are smaller than the critical size of the array in one (right-to-left) flow direction, but larger than the critical size of the array in the other (left-to-right) flow direction.

FIG. 4 is a pair of graphs, consisting of FIGS. 4A and 4B. FIG. 4A is a graph showing simulated normalized velocity flow between two right triangular posts. FIG. 4B is a graph showing normalized velocity profiles through gaps between round obstacles (curve that is symmetrical about Y/Gap=0.5) and right triangularly-shaped obstacles in an array of the type shown in FIG. 1 ($\epsilon$=⅓ radian). In these profiles, vertical lines delineate the areas under each curve into thirds, representing three stream tubes of equal volumetric flow. The curve for the round obstacles demonstrates that one third of the volumetric flow between round obstacles occurs in a stream tube that is adjacent to either obstacle and has a width that is 38% of the gap width. The curve for the triangular obstacles demonstrates that one third of the volumetric flow between triangular occurs in a stream tube that is adjacent to the flat side of one of the two triangular obstacles and has a width that is 42% of the gap width and that an additional one third occurs in a stream tube that is adjacent the sharp side of the pair of triangular obstacles and has a width that is 34% of the gap width.

FIG. 5 is a graph of predicted critical diameter versus the array tilt angle ($\epsilon$) for arrays of triangular (lower line) and circular (upper line) obstacles.

FIG. 6 consists of FIGS. 6A and 6B. FIG. 6A is a schematic diagram of cross-section of a "bump array" device having equilateral triangularly-shaped obstacles disposed in a microfluidic channel. In the figure, fluid flows in the left-to-right direction, as indicated by the arrow marked, "Fluid." In this array, equilateral triangular posts are disposed in a parallelogram lattice arrangement that is tilted with respect directions of fluid flow. Other lattice arrangements (e.g., square, rectangular, trapezoidal, hexagonal, etc. lattices) can also be used. The tilt angle ϵ (epsilon) is chosen so the device is periodic. In this embodiment, a tilt angle of 18.4 degrees (⅓ radian) makes the device periodic after three rows. The tilt angle ϵ also represents the angle by which the array direction is offset from the fluid flow direction. The gap between posts is denoted G with equilateral triangle side length S. Streamlines are shown extending between the posts, dividing the fluid flow between the posts into three regions ("stream tubes") of equal volumetric flow. A relatively large particle (having a size greater than the critical size for the array) follows the array tilt angle when fluid flow is in the direction shown. A relatively small particle (having a size smaller than the critical size for the array) follows the direction of fluid flow. FIG. 6B is a comparison of normalized velocity flow between two equilateral triangular posts (left panel) and normalized velocity flow between two circular posts (right panel). The shaded portions represent an equal proportion of area-under-the-curve, demonstrating that the critical radius for particles flowing past the point of the triangle is significantly smaller (<15% gap width) than the critical radius for particles flowing past the round post (>20% gap width).

DETAILED DESCRIPTION

Figure 1:
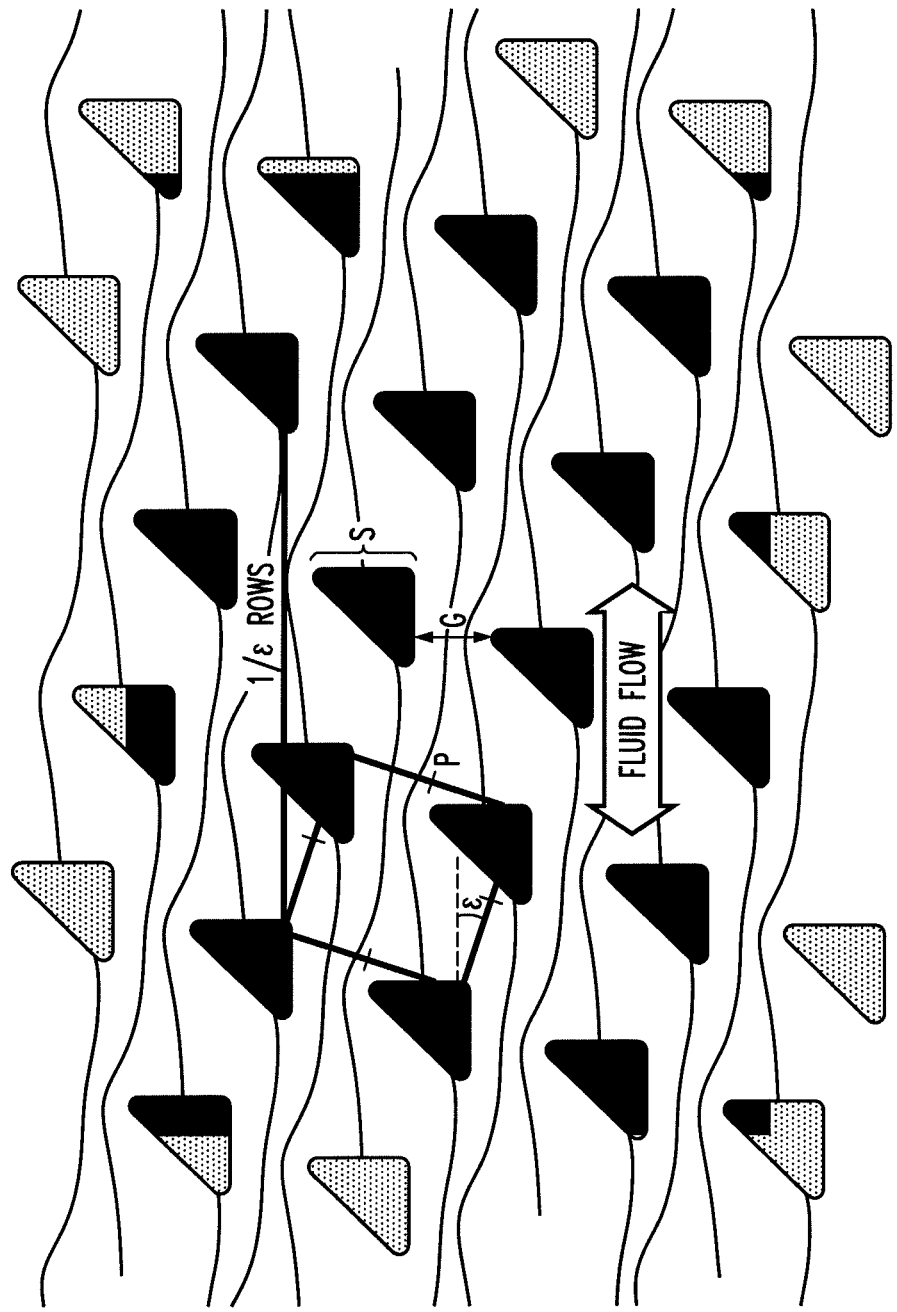

The invention relates to ways of structuring and operating obstacle arrays for separating particles. In previous obstacle arrays described by others, obstacles had shapes and were arranged such that the profile of fluid flow through gaps between adjacent obstacles was symmetrical about the center line of the gap. Viewed another way, the geometry of the adjacent obstacles in such older obstacle arrays is such that the portions of the obstacles defining the gap are symmetrical about the axis of the gap that extends in the direction of bulk fluid flow. The velocity or volumetric profile of fluid flow through such gaps is approximately parabolic across the gap, with fluid velocity and flux being zero at the surface of each obstacle defining the gap (assuming no-slip flow conditions) and reaches a maximum value at the center point of the gap. The profile being parabolic, a fluid layer of a given width adjacent to one of the obstacles defining the gap will contain an equal proportion of fluid flux as a fluid layer of the same width adjacent the other obstacle that defines the gap—meaning that the critical size of particles that are 'bumped' during passage through the gap is equal regardless of which obstacle the particle travels near.

The present invention relates, in part, to the discovery that the particle size-segregating performance of an obstacle array can be improved by shaping and disposing the obstacles such that the portions of adjacent obstacles that deflect fluid flow into a gap between obstacles are not symmetrical about the axis of the gap that extends in the direction of bulk fluid flow. Such lack of flow symmetry into the gap leads to a non-symmetrical fluid flow profile within the gap. Concentration of fluid flow toward one side of a gap (i.e., a consequence of the non-symmetrical fluid flow profile through the gap) reduces the critical size of particles that are induced to travel in the array direction, rather than in the direction of bulk fluid flow. This is so because the non-symmetry of the flow profile causes differences between the width of the flow layer adjacent to one obstacle that contains a selected proportion of fluid flux through the gap and the width of the flow layer that contains the same proportion of fluid flux and that is adjacent the other obstacle that defines the gap. The different widths of the fluid layers adjacent the obstacles defining a gap that exhibits two different critical particle sizes. A particle traversing the gap will be bumped (i.e., travel in the array direction, rather than the bulk fluid flow direction) if it exceeds the critical size of the fluid layer in which it is carried. Thus, it is possible for a particle traversing a gap having a non-symmetrical flow profile to be bumped if the particle travels in the fluid layer adjacent one obstacle, but to be not-bumped if it travels in the fluid layer adjacent the other obstacle defining the gap.

Particles traversing an obstacle array pass through multiple gaps between obstacles, and have multiple opportunities to be bumped. When a particle traverses a gap having a non-symmetrical flow profile, the particle will always be bumped if the size of the particle exceeds the (different) critical sizes defined by the flow layers adjacent the two obstacles defining the gap. However, the particle will only sometimes be bumped if the size of the particle exceeds the critical size defined by the flow layer adjacent one of the two obstacles, but does not exceed the critical size defined by the flow layer adjacent the other obstacle. Particles that do not exceed the critical size defined by the flow layer adjacent either of the obstacles will not be bumped. There are at least two implications that follow from this observation.

First, in an obstacle array in which the obstacles define gaps having a non-symmetrical flow profile, particles having a size that exceeds the smaller of the two critical sizes defined by the flow layers adjacent the obstacles will be separated from particles having a size smaller than that smaller critical size. Significantly, this means that the critical size defined by a gap can be decreased by altering the symmetry of flow through the gap without necessarily decreasing the size of the gap ("G" in FIG. 1). This is important in that decreasing gap size can significantly increase the cost and difficulty of producing the array. Conversely, for a given critical size, the size of the gap defining that critical size can be increased by altering the symmetry of flow through the gap. Because smaller gaps are more likely to clog than larger ones, this is significant for improving the operability of the arrays, allowing greater throughput and lower likelihood of clogging.

Second, in an obstacle array in which the obstacles define gaps having a non-symmetrical flow profile, particles can be separated into three populations: i) particles having a size smaller than either of the critical sizes defined by the flow layers adjacent the obstacles; ii) particles having a size intermediate between the two critical sizes defined by the flow layers adjacent the obstacles; and iii) particles having a size larger than either of the critical sizes defined by the flow layers adjacent the obstacles.

In another aspect of the invention, it has been discovered that decreasing the roundness of edges of obstacles that define gaps can improve the particle size-segregating performance of an obstacle array. By way of example, arrays of obstacles having a triangular cross-section with sharp vertices exhibit a lower critical particle size than do arrays of identically-sized and -spaced triangular obstacles having rounded vertices.

Thus, by sharpening the edges of obstacles defining gaps in an obstacle array, the critical size of particles deflected in the array direction under the influence of bulk fluid flow can be decreased without necessarily reducing the size of the obstacles. Conversely, obstacles having sharper edges can be spaced farther apart than, but still yield particle segregation properties equivalent to, identically-sized obstacles having less sharp edges.

In yet another aspect of the invention, it has been discovered that shaping the obstacles in an obstacle array in such a way that the geometry of the obstacles encountered by fluid flowing through the array in one direction differs (and defines a different critical particle size) from the geometry of the obstacles encountered by fluid flowing through the array in a second direction. For example, fluid flowing through the array illustrated in FIG. 1 in a left-to-right direction encounters and flows around the rounded vertices of the right triangular posts of the array (in this flow direction, the profile of fluid flow through the gaps is asymmetric about the axis of the gaps). However, fluid flowing through the same array in a right-to-left direction encounters and flows around the flat edges of the right triangular posts of the array (in this flow direction, the profile of fluid flow through the gaps is symmetric about the axis of the gaps, being essentially parabolic).

Bump Arrays Having Gaps with Asymmetrical Flow Profiles

This disclosure relates to bump array devices that are useful for segregating particles by size. In one embodiment, the device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles are arranged in rows and columns, in such a configuration that the rows define an array direction that differs from the direction of fluid flow in the flow channel by a tilt angle ($\epsilon$) that has a magnitude greater than zero. The maximum operable value of $\epsilon$ is ⅓ radian. The value of $\epsilon$ is preferably ⅕ radian or less, and a value of ¹⁄₁₀ radian has been found to be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel. That is, the portions of the two obstacles cause assymmetric fluid flow through the gap. The result is that the velocity profile of fluid flow through the gap is asymmetrically oriented about the plane. As a result of this, the critical particle size for particles passing through the gap adjacent to one of the obstacles is different than the critical particle size for particles passing through the gap adjacent to the other of the obstacles.

The materials and number of pieces from which the body is constructed is immaterial. The body can be made from any of the materials from which micro- and nano-scale fluid handling devices are typically fabricated, including silicon, glasses, plastics, and hybrid materials, For ease of fabrication, the flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel. Materials and methods for fabricating such devices are known in the art.

In order to facilitate modeling and predictable operation of the bump array devices described herein, the flow channel is preferably formed between two parallel, substantially planar surfaces, with the obstacles formed in one of the two surfaces (e.g., by etching the surface to remove material that originally surrounded the non-etched portions that remain as obstacles). The obstacles preferably have a substantially constant cross-section along their length, it being recognized that techniques used to fabricate the obstacles can limit the uniformity of the cross section.

The obstacles are solid bodies that extend across the flow channel, preferably from one face of the flow channel to an opposite face of the flow channel. Where an obstacle is integral with (or an extension of) one of the faces of the flow channel at one end of the obstacle, the other end of the obstacle is preferably sealed to or pressed against the opposite face of the flow channel. A small space (preferably too small to accommodate any of particles of interest for an intended use) is tolerable between one end of an obstacle and a face of the flow channel, provided the space does not adversely affect the structural stability of the obstacle or the relevant flow properties of the device. In some embodiments described herein, obstacles are defined by a cross-sectional shape (e.g., round or triangular). Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

As described herein, certain advantages can be realized by forming obstacles having sharp (i.e., non-rounded) edges, especially at the narrowest part of a gap between two obstacles. In order to take advantage of the benefits of sharp edges, a skilled artisan will recognize that certain microfabrication techniques are preferable to others for forming such edges. Sharpness of edges can be described in any of a number of ways. By way of example, the radius of curvature of an edge (e.g., the vertex of a triangular post) can be measured or estimated and that radius can be compared with a characteristic dimension of the obstacle (e.g., the shorter side adjacent the vertex of a triangular, square, or rectangular post, or the radius of a round post having a pointed section). Sharpness can be described, for example, as a ratio of the radius of curvature to the characteristic dimension. Using equilateral triangular posts as an example, suitable ratios include those not greater than 0.25, and preferably not greater than 0.2.

The number of obstacles that occur in an array is not critical, but the obstacles should be sufficiently numerous that the particle-separating properties of the arrays that are described herein can be realized. Similarly, other than as described herein, the precise layout and shape of the array is not critical. In view of the disclosures described herein, a skilled artisan in this field is able to design the layout and number of obstacles necessary to make bump arrays capable of separating particles, taking into account the sizes and identities of particles to be separated, the volume of fluid in which the particles to be separated are contained, the strength and rigidity of the materials used to fabricate the array, the pressure capacity of fluid handling devices to be used with the array, and other ordinary design features.

As discussed herein, the shape and spacing of obstacles are important design parameters for the arrays. The obstacles are generally organized into rows and columns (use of the terms rows and columns does not mean or imply that the rows and columns are perpendicular to one another). Obstacles that are generally aligned in a direction transverse to fluid flow in the flow channel are referred to as obstacles in a column. Obstacles adjacent to one another in a column define a gap through which fluid flows. Typically, obstacles in adjacent columns are offset from one another by a degree characterized by a tilt angle, designated $\epsilon$ (epsilon). Thus, for several columns adjacent one another (i.e., several columns of obstacles that are passed consecutively by fluid flow in a single direction generally transverse to the columns), corresponding obstacles in the columns are offset from one another such that the corresponding obstacles form a row of obstacles that extends at the angle $\epsilon$ relative to the direction of fluid flow past the columns. The tilt angle can be selected and the columns can be spaced apart from each other such that $1/\epsilon$ (when $\epsilon$ is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of $\epsilon$.

The shape of the individual obstacles is important, and it has been discovered that improved bump array function can be achieved by shaping one or more portions of two obstacles that define a gap in such a way that the portions of the obstacles that are upstream from, downstream from, or briding (or some combination of these, with reference to the direction of bulk fluid flow through the flow channel) the narrowest portion of the gap between the obstacles are asymmetrical about the plane that bisects the gap and is parallel to the direction of bulk fluid flow. Both for simplicity of fabrication and to aid modeling of array behavior, all obstacles in an array are preferably identical in size and shape, although this need not be the case. Furthermore, arrays having portions in which obstacles are identical to one another within a single portion, but different than obstacles in other portions can be made.

Without being bound by any particular theory of operation, it is believed that asymmetry in one or more portions of one or both of the obstacles defining a gap leads to increased fluid flow on one side or the other of the gap. A particle is bumped upon passage through a gap only if the particle exceeds the critical particle size corresponding to the gap. The critical particle size is determined by the density of fluid flux near the boundaries of the gap (i.e., the edges of the obstacles that define the gap). Increased fluid flow on one side of a gap (i.e., against one of the two obstacles defining the narrowest portion of the gap) intensifies flux density near that side, reducing the size of the particle that will be bumped upon passage through that side of the gap.

In one embodiment of the device, the shape of each of multiple obstacles in a column is substantially identical and symmetrical about the plane that bisects each of the multiple obstacles. That is, for any one column of obstacles, the geometry encountered by particles traveling in fluid flowing through the gaps between the obstacles in the column is identical when the fluid is traveling in a first direction and when the fluid is travelling in a second direction that is separated from the first direction by 180 degrees (i.e., flow in the opposite direction).

In another important embodiment, the geometry encountered by particles traveling in fluid flowing through the gaps between the obstacles in the column is different when the fluid is traveling in a first direction than the geometry encountered when the fluid is travelling in a second direction that is different from the first direction by 90-180 degrees. In this embodiment, fluid flow can, for example, be oscillated between the two flow directions, and the particles in the fluid will encounter the different obstacle geometry. If these geometrical differences result in different fluid profiles through the gaps (compare the panels in FIG. 6B, for example), then the gap can exhibit different critical particle sizes in the two directions. If a gap exhibits different critical sizes for flow in the two directions, then the populations of particles that will be bumped upon passing through the gap will differ depending on the direction of flow. This difference in the populations bumped in the two directions can be used to effect segregation of the differently-acting particles.

For example, consider a gap that exhibits a first critical size for bulk fluid flow in one direction, but exhibits a different critical size for bulk fluid flow in a second direction. For fluid flow in the first direction, particles having a size greater than the first critical size will be bumped, and particles having a size less than the first critical size will not be bumped. Similarly, for fluid flow in the second direction, particles having a size greater than the second critical size will be bumped, and particles having a size less than the second critical size will not be bumped. If flow is oscillated between the first and second directions, then particles having a size larger than both the first and the second critical sizes will be bumped in both directions. Similarly, particles having a size smaller than both the first and the second critical sizes will not be bumped in either direction. For these two populations of particles, flow oscillations of approximately equal quantities in both directions will leave these particles substantially at their initial position. However, particles having a size intermediate between the two critical sizes will be bumped when bulk fluid flow is in one direction, but will not be bumped when bulk fluid flow is in the other direction. Thus, when flow oscillations of approximately equal quantities in both directions are performed, these particles will not be left in their initial position, but will instead have been displaced from that original position by an amount equal to (the size of an obstacle+the gap distance G)×the number of oscillations. In this way, these particles (the ones having a size intermediate between the two critical sizes) can be segregated from the other particles with which they were initially intermixed.

In the special case of when the first and second directions differ by 180 degrees (i.e., the flows are in opposite directions, the particles having a size intermediate between the two critical sizes will be displace at an angle of 90 degrees relative to the direction of oscillating flow.

The behavior of particles in a bump array is not a function of the absolute direction in which the particles (or the fluid in which they are suspended) move, but rather is a function of the array geometry that the particles encounter. As an alternative to operating a bump array with alternating flow between first and second directions, the same particle-displacing effects can be obtained using flow only in the first direction by increasing the size of the array by two times the number of oscillations, maintaining one portion of the array in its original arrangement, but altering the second portion of the array such that the geometry of the array is identical to the geometry encountered by particles in fluid moving in the second direction in the original array (even though the fluid moves in the first direction only. Using the array illustrated in FIG. 1 by way of example, the same displacement effects on particles can be obtained by two oscillations of flow in this array (i.e., two units of flow left-to-right and two units of flow right-to-left) as can be obtained by four units of left-to-right flow through an array having four times the (left-to-right) length of the array in FIG. 1, so long as two lengths of the array are arranged as shown in FIG. 1 and two lengths of the array are arranged as the mirror image (left-to-right) of the array shown in FIG. 1.

Priority Application Text

One or more aspects of the invention disclosed herein was previously described in U.S. provisional application 61/135,854. The relevant text of that application (as well as additional description) is included in this section.

The invention relates to a microfluidic device designed to separate objects on the basis of physical size. The objects can be cells, biomolecules, inorganic beads, or other objects of round or other shape. Typical sizes fractionated to date range from 100 nanometers to 50 micrometers, although smaller or larger sizes are possible. Prior work with these arrays involved continuous flows in one direction, and particles are separated from the flow direction by an angle which is a monotonic function of their size.

This invention is a modification on bump array design that adds functionality. By changing the shape of the posts from circles to a shape that is asymmetric about an axis parallel to the fluid flow, two new functionalities may be added:

1. The critical particle size for bumping may be different depending on which direction a particle moves through the array. This has been experimentally verified with right triangular posts, and extends to arbitrary shapes that are asymmetric about the flow axis.

2. With such designs, the angle of displacement from the fluid flow of particles may be designed not to be monotonic—e.g. peaked at a certain particle size.

Such bump arrays have multiple uses, including all of the uses for which bump arrays were previously known.

The device can be used to separate particles in a selected size band out of a mixture by deterministic lateral displacement. The mechanism for separation is the same as the bump array, but it works under oscillatory flow (AC conditions; i.e., bulk fluid flow alternating between two directions) rather than continuous flow (DC conditions; i.e., bulk fluid flow in only a single direction). Under oscillatory flow, particles of a given size range can be separated perpendicularly from an input stream (perpendicular to the alternating flow axis when the alternating flows differ in direction by 180 degrees) without any net displacement of the bulk fluid or net displacement of particles outside the desired range. Thus, by injecting a sample including particles of the given range into an obstacle array and thereafter alternating fluid flow through the obstacle array in opposite directions (i.e., in directions separated from one another by 180 degrees), particles that are exceed the critical size in one flow direction but do not exceed the critical size in the other flow direction can be separated from other particles in the sample by the bumping induced by the array. Such particles are bumped (and follow the array direction) when fluid flows in one direction, but are not bumped (and follow the bulk fluid flow direction) when fluid flows in the opposite direction. Particles that do not exceed the critical size in either flow direction will not be bumped by the array (will follow the bulk fluid in both directions), and will remain with the sample bolus. Particles that exceed the critical size in both flow directions will be bumped by the array (will follow the array direction) when fluid flows in one direction, and are also bumped (will follow the array direction in the opposite direction) when fluid flows in the opposite direction, and will therefore remain with the sample bolus.

That is, in devices of this sort, critical particle size depends on direction of fluid flow. Intermediate sized particles can be made to ratchet up a device under oscillatory flow.

Second, in a continuous flow mode, particles of a desired size can be induced to move to one side of a fluid stream, and particles above or below that size to the other side or not displaced at all. Thus collection of desired particles may be easier. In conventional devices, particles above a desired range are also displaced from the fluid flow to the same side of the flow, so separating the desired from undesired larger ones may be harder. In this embodiment, obstacles defining different critical sizes for fluid flow in opposite directions are employed in two configurations that are mirror images of one another. For example, with reference to FIG. 1, such an array would include right triangular posts arranged as shown in FIG. 1 (i.e., hypotenuse sloping from lower right to upper left and the tilt angle ϵ extending from the horizontal toward the bottom of the figure) and would also include right triangular posts arranged as they would appear in a mirror held perpendicularly at the right or left side of the array shown in FIG. 1 (i.e., right triangular posts having their hypotenuse sloping from upper right to lower left and the tilt angle ϵ extending from the horizontal toward the top of the figure). Particle separation achieved by bulk fluid flow in a single direction (i.e., either from left-to-right or right-to-left) through such an array would be equivalent to back-and-forth flow through the array illustrated in FIG. 1. Particles in the selected size range would be bumped toward the top of the array (as shown in FIG. 1), while particles having larger or smaller sizes would remain at the vertical level at which they enter the array (assuming approximately equal numbers of obstacles in each of the two configurations are encountered).

We have also discovered that reduction in critical particle size as a ratio of gap, compared to circular posts, occurs when particles bump off sharp edges. This allows larger separation angle without fear of clogging the device—faster separations.

These developments potentially reduces the necessary chip area compared to a continuous flow bump array.

Device is a microfabricated post array constructed using standard photolithography. A single mask layer is etched into silicon or used to make a template for PDMS molding. Post arrays are usually sealed with a PDMS coated cover slip to provide closed channels.

The new methods may require more careful control of the post shape than a conventional device. Oscillatory flow operation may require more complicated fluid control drivers and interfaces than continuous flow operation.

Both aspects of the invention have been experimentally verified in bump array with right triangular posts.

Figure 11:
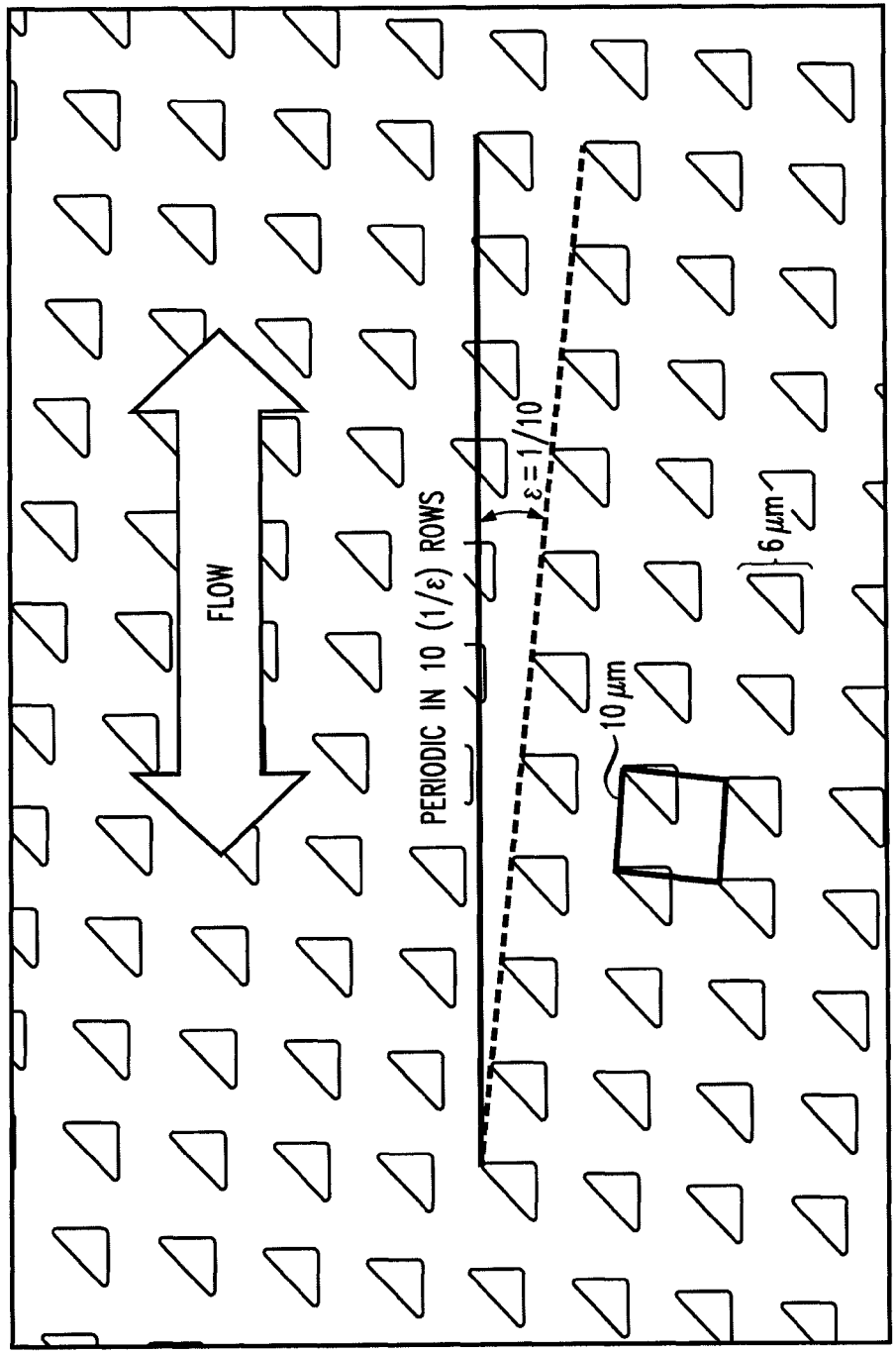
FIG. 11 is an image of an array constructed as described herein.

See attached slides:

FIG. 11 is a scanning electron microscope image of posts in an obstacle array of the type described herein. Right isosceles triangular posts, 6 microns on a side, were placed on a square lattice with spacing of 10 microns, giving a gap of approximately 4 microns. The square lattice was tilted 5.71 degrees (0.1 radians) with respect to the device sidewalls to provide necessary asymmetry. Fluid flows along the horizontal axis.

In FIG. 1, the total fluid flux through each gap can be divided into $n=1/\epsilon'$ flow streams (stream tubes), where n is a whole number. Each flow stream carries equal fluid flux, shown schematically in FIG. 1 for n=3. The stream tubes are separated by stall lines, each stall line beginning and ending on a post. The stream tubes shift their positions cyclically so that after n rows each streamline returns to its initial position within the gap.

The width of the stream closest a post determines the critical particle size. If the particle's radius is smaller than the width of the stream, then the particle's trajectory is undisturbed by the posts and travels in the same direction of the flow. If the particle's radius is larger than the width of the closest stream, then it is displaced across the stall line and it's trajectory follows the tilted axis of the array (i.e., the array direction).

The width of the stream closest to the post can be determined by assuming that the velocity profile through a gap is parabolic—the case for fully-developed flow in a rectangular channel. Since each stream carries equal flux and there are n streams, we can integrate over the flow profile such that the flux through a stream of width Dc/2 (Dc is the critical diameter of a particle) closest to the post is equal to the total flux through the gap divided by n. That is, the integral from 0 to Dc/2 of u(x)dx (u being a function of flux at any position x within the gap) being equal to 1/n times the integral of u(x)dx over the entire gap.

Thus, the critical particle size can be determined from the flow profile. For the case of circular posts, a parabolic flow profile closely approximates the flow profile through the gap and the critical particle size can be determined analytically.

Figure 4A:
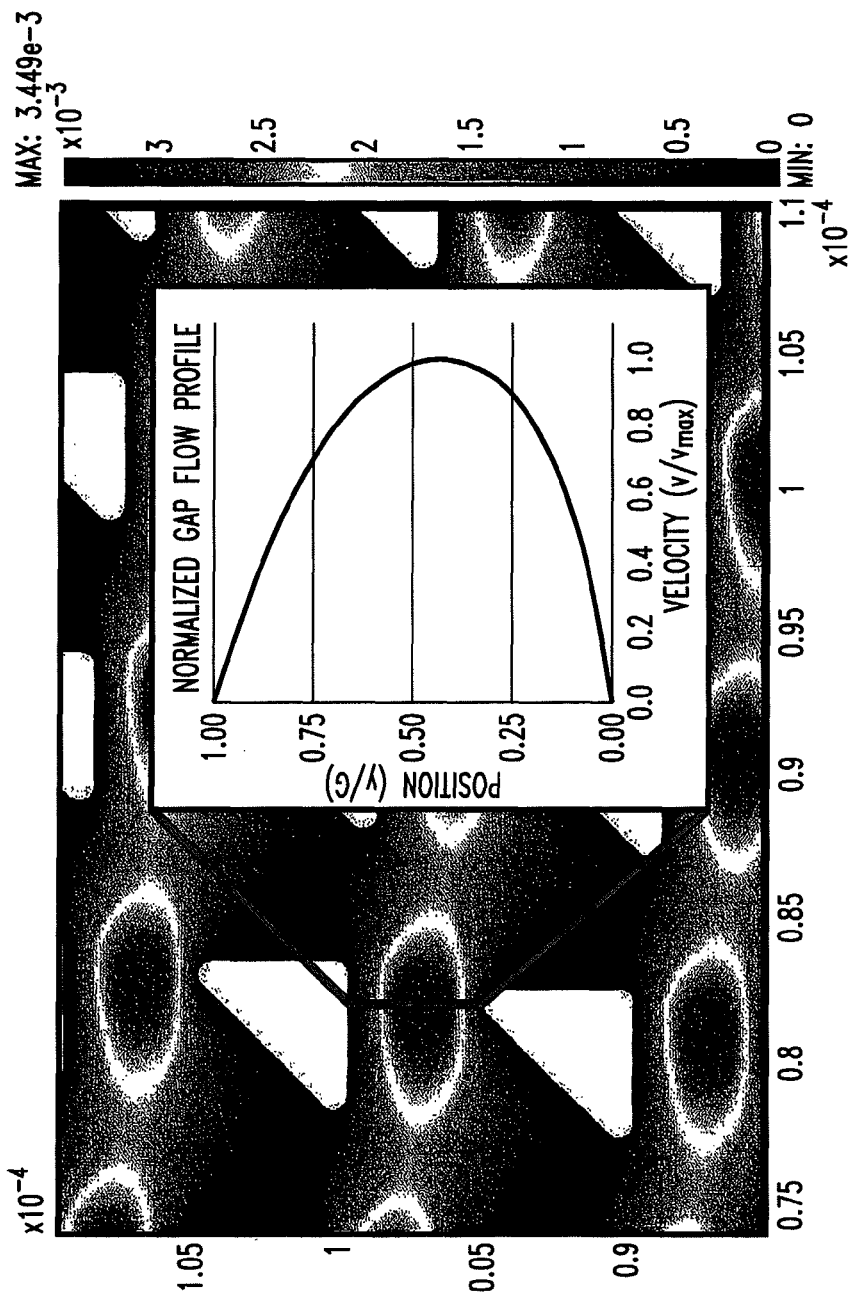

FIG. 4A shows a numerical simulation of flow profile for an array of triangular posts. We cannot assume that flow profile through triangular posts is parabolic because of the broken symmetry. Therefore, flow profile through gap of triangular posts was extracted from numerical simulation (program—COMSOL) of flow through an array with same size and spacing as devices actually made.

Figure 4B:
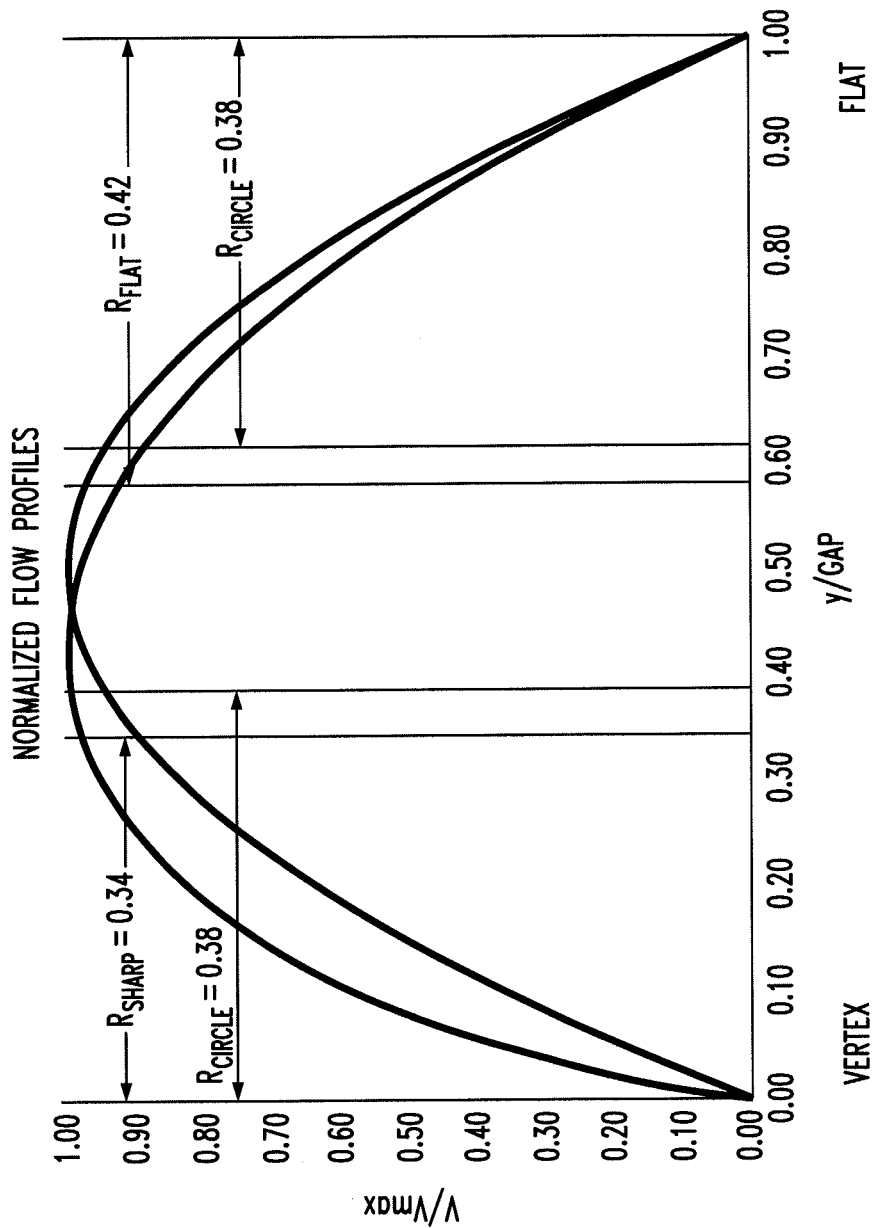

FIG. 4B illustrates a comparison of velocity flow profiles between circular and triangular posts. Normalized velocity profiles through gap for triangular and circular posts are shown. As shown, the flow profile for the triangle posts is asymmetric about the center of the gap; more fluid flows along the vertex of the triangle than along the flat edge.

Figure 12:
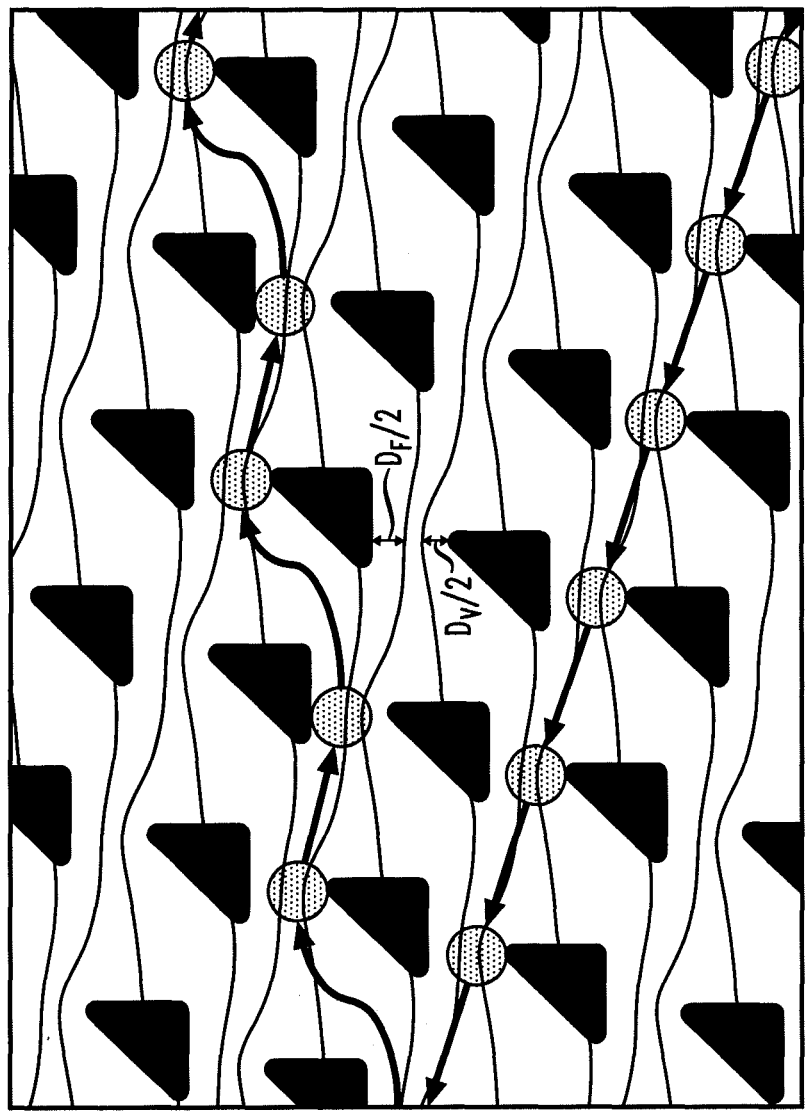
FIG. 12 illustrates particle motion in a ratchet bump array of the type described herein.
Figure 13:
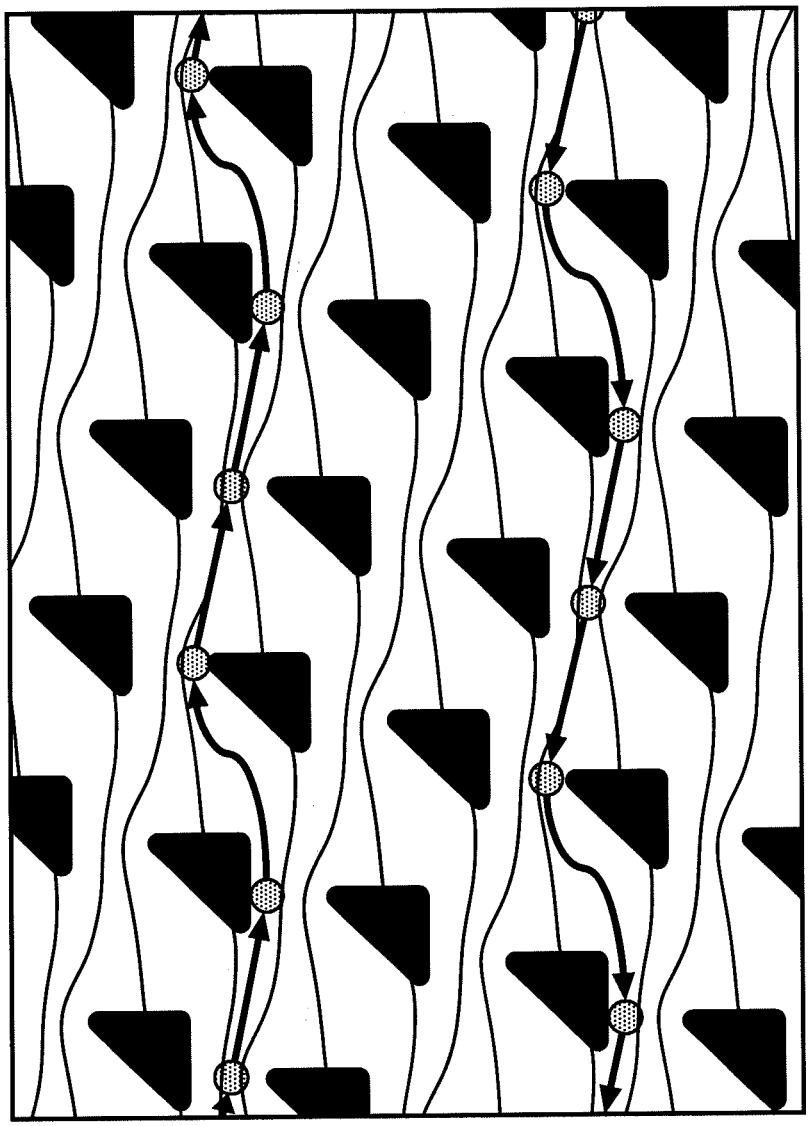
FIG. 13 illustrates particle motion in a ratchet bump array of the type described herein.
Figure 14:
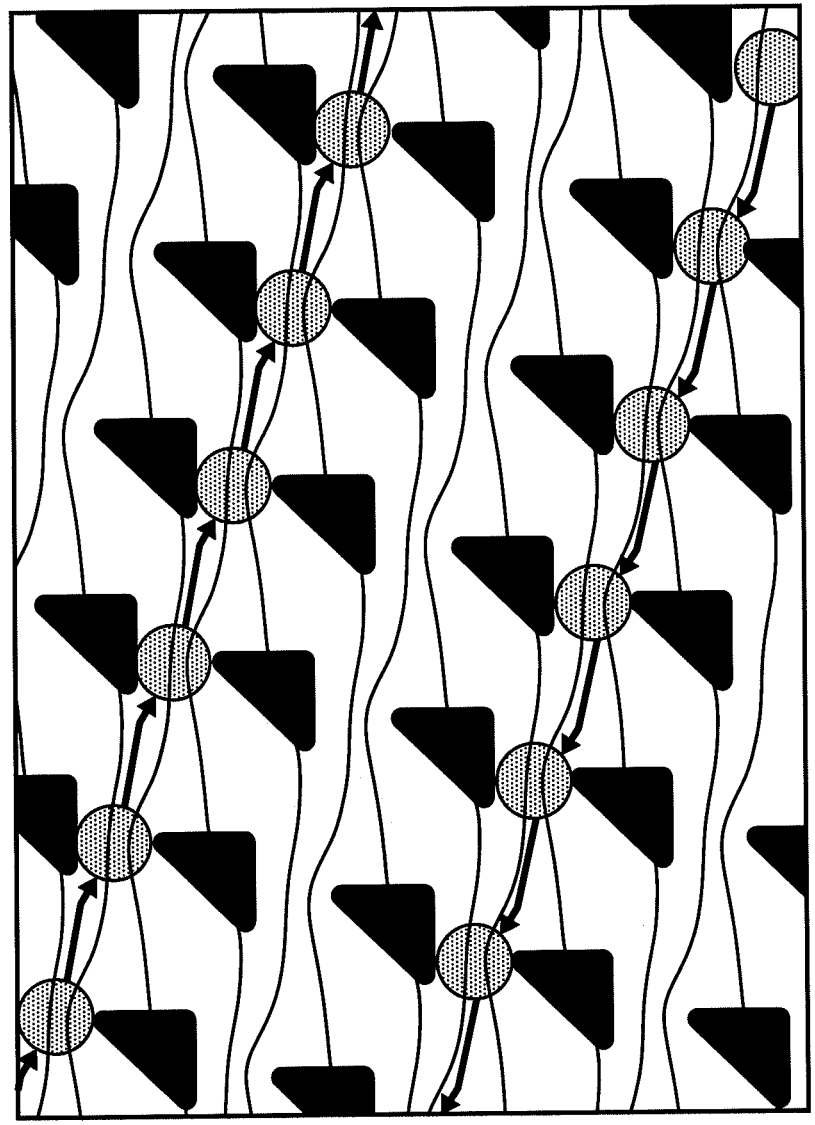
FIG. 14 illustrates particle motion in a ratchet bump array of the type described herein.

FIGS. 12-14 illustrate particle motion in a ratchet bump array of the type described herein. When particles move through the array, the side of the post they interact with depends on which direction they are moving in the array. In this case, when the particles are moving from right-to-left, they bump off the flat edge of the triangular posts. When the particles are moving from left-to-right, they bump off the sharp vertex of the triangular posts. Thus, since the flow profile is asymmetric, we cannot expect particles to follow the same trajectory when travelling in both directions through the array.

Figure 15:
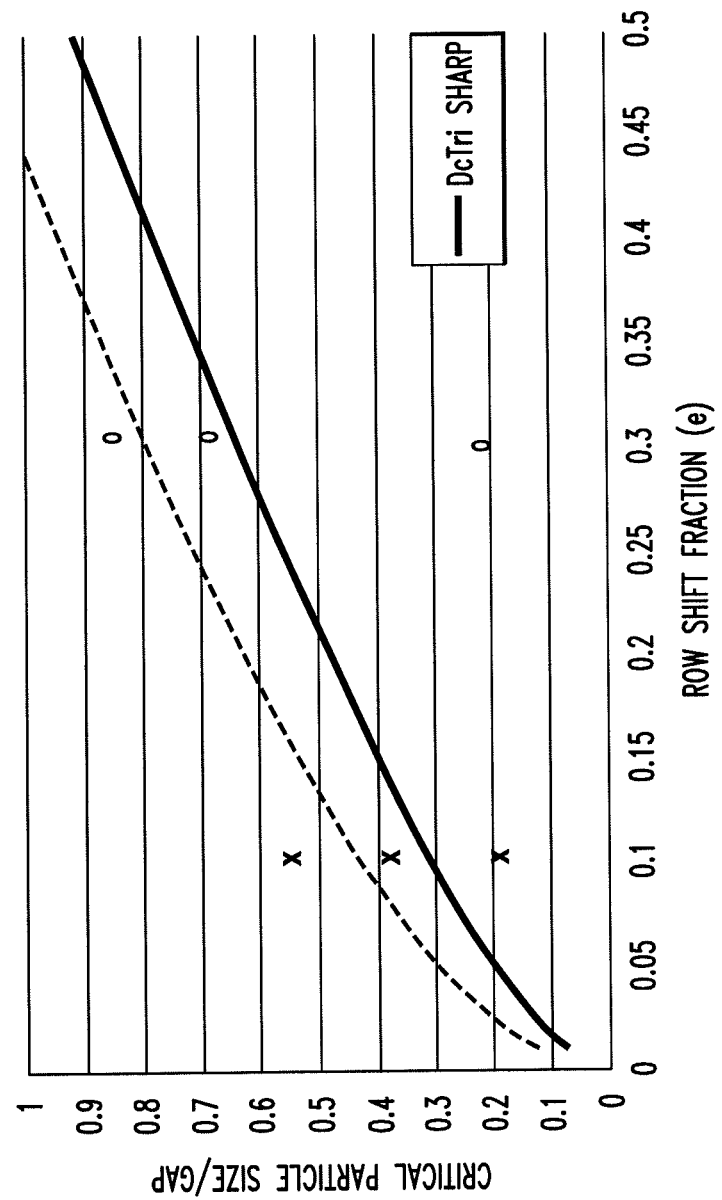
FIG. 15 is a graph comparing the critical size characteristics of round and triangular posts.

Critical Particle Size for Triangular Posts—Employing the same kind of analysis described in the Inglis et al., 2006, Lab Chip 6:655-658, we can integrate over the flow profile to find the width of characteristic streams. However, since the flow profile is asymmetric about the center of the gap, the stream width, and hence the critical particle size will be different depending on which side we examine. As shown in FIG. 4B, the result of the asymmetry introduced by the triangular posts is that the critical particle size is different depending on which side of the triangular obstacle particles interact with. If they are moving along the sharp vertex, then the critical particle size is smaller than if they are moving along the flat edge. Critical particle size vs. array angle ($\epsilon$) are plotted in FIG. 15 compared to circular posts. The critical particle size for bumping along the sharp vertex of the triangle is substantially smaller than for that of circular posts or the flat edge. This allows higher angles of separation to be used without fear of clogging the devices. When the particle diameter is larger than the gap size (G in FIG. 1), there is substantial risk that the array will become clogged if particle density is high.

Figure 3A:
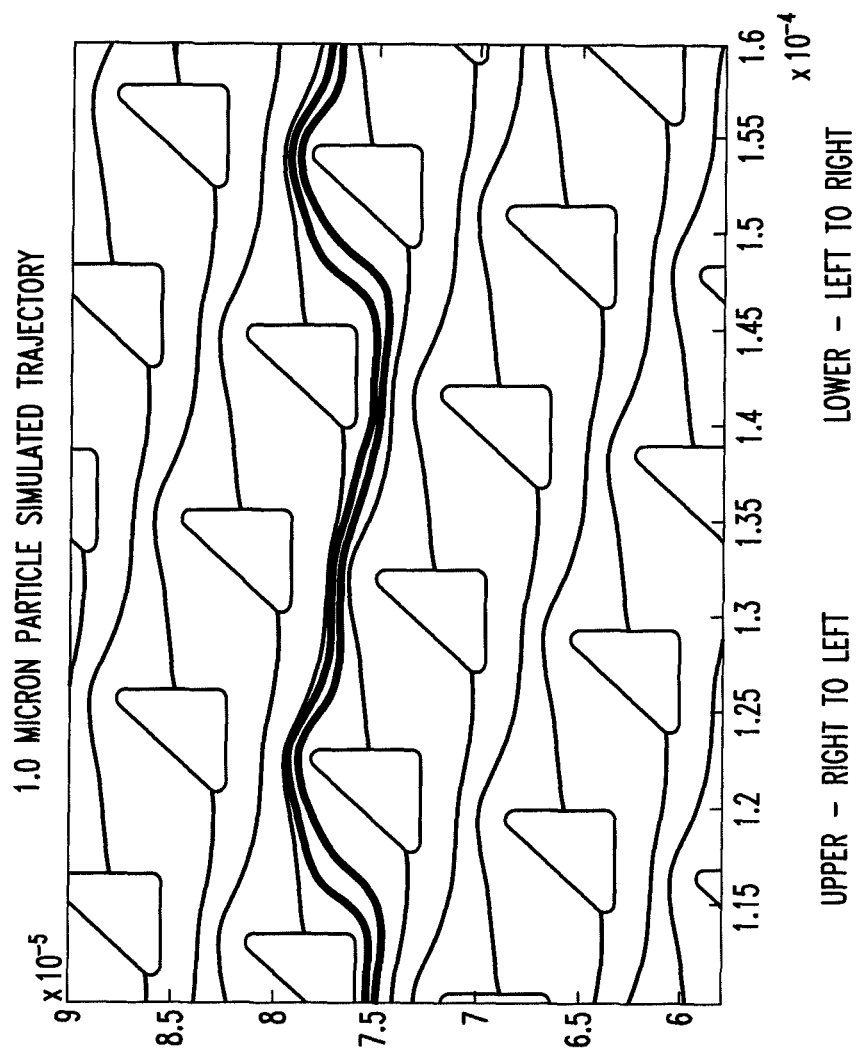
Figure 3B:
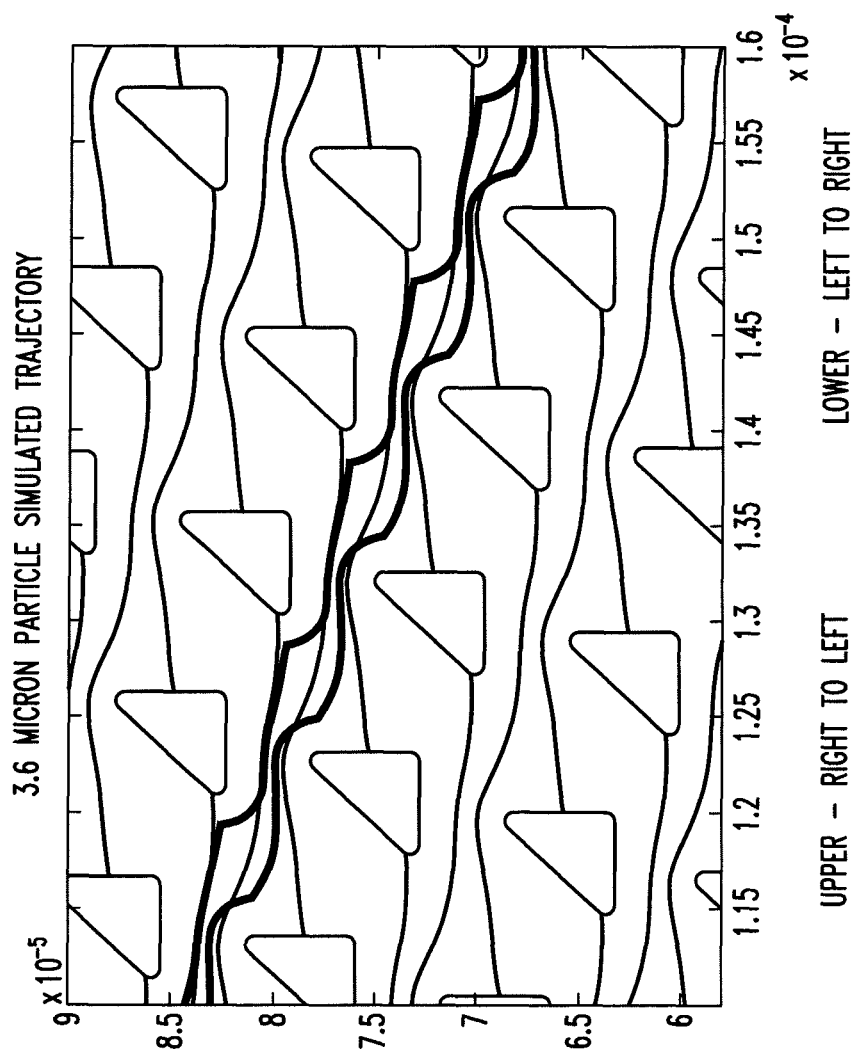

FIGS. 3A-3C illustrate representative particle behavior in a ratchet bump array. For a device constructed as shown in FIG. 11, three representative particles were chosen for this illustration. One particle (illustrated in FIG. 3B) was chosen larger than both critical particle sizes (i.e., larger than the critical particle sizes defined by right-to-left and left-to-right fluid flows). One particle (illustrated in FIG. 3A) was chosen smaller than both critical particle sizes. Finally, one particle (illustrated in FIG. 3C) was chosen in the intermediate range—smaller than the critical particle size (DF in FIG. 12) along the flat edge, but larger than the critical particle size (DV in FIG. 12) along the sharp edge. These figures illustrate the behavior of particles that were put into the device and their trajectory under oscillatory flow was observed.

Large Particle (FIG. 3B): Since the particle is larger than the critical particle size along both edges, it follows the array tilt axis ($\epsilon$) in both directions and shows no net displacement under oscillatory flow.

Small Particle (FIG. 3A): Since the particle is smaller than the critical particle size along both edges, it follows the fluid trajectory in both directions and shows no net displacement.

Intermediate Particle (FIG. 3C): When the particle moves to the right, it bumps off the flat edge of the triangular posts. Since it is smaller than the critical particle size (DF), it follows the fluid trajectory. When the particle moves to the left, it bumps off the sharp vertex of the triangular posts. Since it is larger than the critical particle size on this side (DV), it follows the array tilt axis and is displaced upward. As shown, under oscillatory flow, particles in the intermediate range are displaced perpendicular to the direction of the flow. After three cycles of moving back and forth, the bulk fluid has not been displaced, but the particle has moved over 200 microns.

If all three particle types were mixed and placed in a single array under oscillatory flow (i.e., fluid flow oscillating between the right-to-left and left-to-right directions), the intermediate particles would be displaced toward the top of these figures while the small and large particles would have no net motion.

In FIGS. 12-14, representations of intermediate, small, and large particles (respectively) were overlaid on top of numerical simulation of stream tubes to show motion of particles more clearly. n=1/ϵ was chosen to be 3 to allow periodicity to be more easily seen.

When intermediate particles (FIG. 12) travel along the sharp edge, they bump like expected. However, when the particles travel along the flat edge, their motion is different than that of the small particles. When they perform their characteristic zig to keep going with the direction of the fluid, they are too large to stay in that stream that is close to the sharp vertex and are displaced across the first stall line. The result is that their motion is periodic in two rows instead of three. With any other tilt angle, the motion is similar and the periodicity is n−1. The result of this n−1 periodicity is that the intermediate sized particles are actually displaced against the axis tilt angle. Thus a mixture of large, small and intermediate particles will be separated into three streams. Small particles will go straight through (see FIG. 13). Large particles will follow the array tilt axis (see FIG. 14). Intermediate particles will follow a separate path that is dependent on the post geometry.

The applications for which devices described herein are useful include the same ones described in the Huang patent (U.S. Pat. No. 7,150,812): biotechnology and other microfluidic operations involving particle separation.

Continuous-flow fractionation of small particles in a liquid based on their size in a micropost "bump array" by deterministic lateral displacement was demonstrated previously (e.g., Huang et al., 2004, Science 304:987-990). The ratchet bump array described herein possesses all the same advantages of the previous work, but adds two new functionalities:

First, the devices can be used to separate particles in a selected size band out of a mixture by deterministic lateral displacement under oscillatory flow (AC conditions) rather than continuous flow (DC conditions). Under oscillatory flow, particles of a given size range can be separated perpendicularly from an input stream (perpendicular to the AC flow axis) without any net displacement of the bulk fluid or particles outside the desired range.

Second, in continuous flow mode, the device exhibits tri-modal behavior. Particles of a desired size range can be induced to move to one side of a fluid stream, and particles above or below that size to the other side or not displaced at all. Thus collection of these desired particles may be easier. In conventional devices, the devices were bimodal and all particles above a desired size range are displaced from the fluid flow to the same side of the flow, so separating the desired from undesired larger ones requires multiple stages whereas the ratchet bump array requires only one.

Definitions

As used herein, each of the following terms has the meaning associated with it in this section.

The terms "bump array" and "obstacle array" are used synonymously herein to describe an ordered array of obstacles that are disposed in a flow channel through which a particle-bearing fluid can be passed.

A "substantially planar" surface is a surface that has been made about as flat as a surface can be made in view of the fabrication techniques used to obtain a flat surface. It is understood that no fabrication technique will yield a perfectly flat surface. So long as non-flat portions of a surface do not significantly alter the behavior of fluids and particles moving at or near the surface, the surface should be considered substantially planar.

In a bump array device, "fluid flow" and "bulk fluid flow" are used synonymously to refer to the macroscopic movement of fluid in a general direction across an obstacle array.

These terms do not take into account the temporary displacements of fluid streams that are necessitated in order for fluid to move around an obstacle in order for the fluid to continue to move in the general direction.

In a bump array device, the tilt angle ϵ is the angle between the direction of bulk fluid flow and the direction defined by alignment of rows of sequential (in the direction of bulk fluid flow) obstacles in the array. This angle is illustrated in FIGS. 1, 6, and 11, for example.

In a bump array device, the "array direction" is a direction defined by the defined by alignment of rows of sequential (in the direction of bulk fluid flow) obstacles in the array.

A "critical size" of particles passing through an obstacle array is a parameter that describes the size limit of particles that are able to follow the laminar flow of fluid nearest one side of a gap through which the particles are travelling when flow of that fluid diverges from the majority of fluid flow through the gap. Particles larger than the critical size will be 'bumped' from the flow path of the fluid nearest that side of the gap into the flow path of the majority of the fluid flowing through the gap. In a bump array device, such a particle will be displace by the distance of (the size of one obstacle+the size of the gap between obstacles) upon passing through the gap and encountering the downstream column of obstacles, while particles having sizes lower than the critical size will not necessarily be so displaced. Significantly, when the profile of fluid flow through a gap is symmetrical about the plane that bisects the gap in the direction of bulk fluid flow, the critical size will be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. Of course, the size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

A particle is "bumped" in a bump array if, upon passing through a gap and encountering a downstream obstacle, the particle's overall trajectory follows the array direction of the bump array (i.e., travels at the tilt angle ϵ relative to bulk fluid flow). A particle is not bumped if its overall trajectory follows the direction of bulk fluid flow under those circumstances. Conceptually, if flow through a gap is visualized as being composed of multiple individual layers of fluid (i.e., stream tubes, if thought of in a cross-section of fluid flowing through the gap), a particle is "bumped" if the particle is displaced by a post out of its incident flow tube into an adjacent flow tube as it traverses a gap bounded by the post.

"The direction of bulk fluid flow" in an obstacle array device refers to the average (e.g., macroscopic) direction of fluid flow through the device (i.e., ignoring local flow deviations necessitated by flow around obstacles in the fluid channel).

EXAMPLES

The subject matter of this disclosure is now described with reference to the following Examples. These Examples are provided for the purpose of illustration only, and the disclosure is not limited to these Examples, but rather encompasses all variations which are evident as a result of the teaching provided herein.

Example 1

A Deterministic Microfluidic Ratchet

This example describes a microfluidic device in which the trajectory of particles within a certain size range varies with the direction the particles move through the device. This ratcheting effect is produced by employing triangular rather than the conventional circular posts in a deterministic lateral displacement device where an array of posts selectively displaces particles as they move through the array. This effect is then used to demonstrate a fractionation technique where particles can be separated from a fluid plug without any net motion of the original fluid plug. The underlying mechanism of this method is based on an asymmetric fluid velocity distribution through the gap between posts.

Microfluidic devices, such as those used in "lab on a chip" applications, typically operate at low Reynolds number ("low" Reynolds number refers to Reynolds number not greater than 1, and preferably smaller, such as 0.1, $10^{-3}$, or smaller). In this regime, the fluid flow through an arbitrary geometry can be considered to be time-invariant-reversing the applied pressure gradient that drives the fluid will reverse the flow field because inertial effects are negligible. At high Peclet number ("high" Peclet number refers to Peclet number greater than 1, and preferably much greater, such as 10, 100, or more), this can be extended to say that diffusive effects can be ignored and objects in the fluid will deterministically flow along a stream tube unless some other interaction, such as displacement by steric repulsion from a channel wall, disrupts their path and moves them to an adjacent stream tube. The degree to which the particle trajectory is shifted from its original path depends directly on its size; larger particles will be displaced farther than smaller particles and will consequently follow different stream tubes as they progress through the device. This phenomenon, which we call deterministic lateral displacement, has been used in several schemes to perform microscale particle separations.

The "bump array" is a microfluidic device that relies on deterministic lateral displacement to separate particles with high resolution. This device relies on asymmetric bifurcation of fluid streams in a post array that is tilted at an angle $\epsilon$ (epsilon; typically on the order of 0.1 radians) with respect to the direction of the overall fluid flow. The fluid flowing through a gap splits around a post in the next row, with $1-\epsilon$ of the fluid going through the gap on one side of the next post, while the other $\epsilon$ of fluid goes around the other side of the next post. As a result, the fluid motion can be characterized by $1/\epsilon$ streams that cycle through positions in the gap, but travel straight on average. If a particle suspended in the fluid is small compared to the width of a stream in a gap, the posts will not affect it as it moves through the array and it will travel straight with the fluid flow. However, if the particle is large relative to the width of a stream, it will be displaced into an adjacent stream when the stream it occupies is nearest a post as it moves through a gap. Because of the cyclical way the streams move through gaps, this displacement or "bump" will occur at every row and the particle will travel at an angle with respect to the fluid and other small particles. With a sufficiently long device, significant separation can be obtained between large and small particles.

Figure 2:
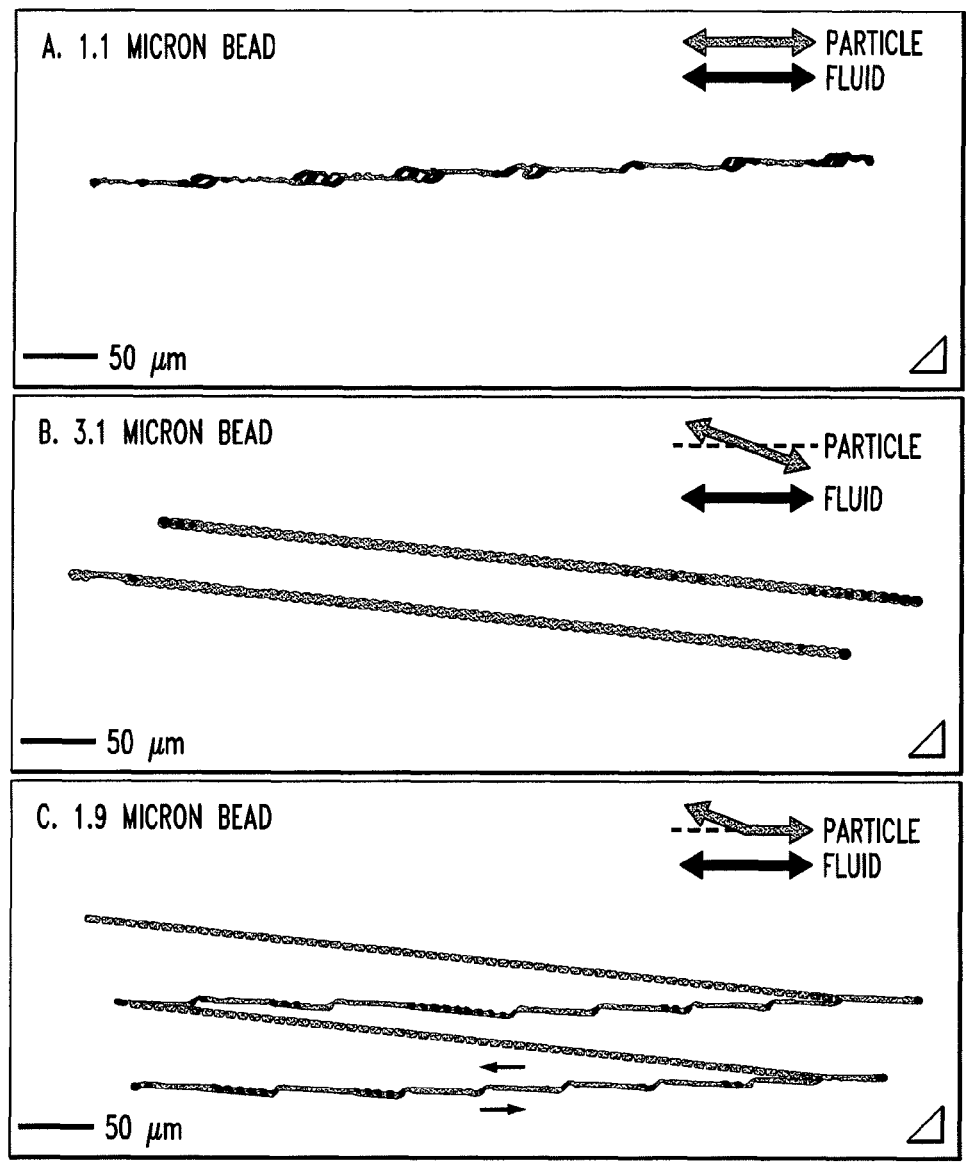

FIG. 2A shows a time fluorescent time-lapse image of a small particle (1.1 micron diameter polystyrene bead) flowing through such an array at a typical speed of 100 microns/sec. As the particle moves forward, it takes many small steps parallel to the array axis as it moves through, followed by one larger step perpendicular to the motion of the fluid (in what we refer to as "zig-zag mode"), so that the overall motion is to follow the plug of fluid which originally contained the particle. In taking the image of FIG. 2A, the fluid flow was cycled back and forth (by reversing the pressure) twice. The particle retraced its path, as expected from flows at low Reynolds and high Peclet number in a deterministic device not relying on diffusion.

FIG. 2B shows a similar image but for a larger particle (3.1 microns). In this case the particle clearly follows the array axis (i.e., travels in the array direction) and not the fluid flow. Because the particle is displaced from its flow path by the posts in each row, we refer to this as "bumping mode." This difference in flow direction as a function particle size has been exploited to make fractionation devices for both polystyrene beads as well as biological particles. As in FIG. 2A, the time lapse image shows the path of the particle over two cycles of flowing forward and back, and again the path of the particles is reversible (i.e., the particles end up where they began).

FIG. 2C shows the same experiment in the same array for a particle of intermediate size (1.9 microns). The results are very different than those shown if FIGS. 2A and 2B. This particle "zig-zags" when going to the right (i.e., moving from left-to-right) to follow the fluid flow but "bumps" when going to the left to follow the post array axis. Its path is not reversed when the fluid flow direction is reversed, with the net result that such particles are separated from a plug of fluid in a perpendicular direction when the fluid is subjected to an oscillatory flow.

The displacement of a particle off of a post is an inherently irreversible interaction, but particle trajectories in a circular post bump array are ostensibly reversible because of symmetry. There is no controversy in this statement for small particles which follow the fluid because the fluid flow must be reversible in the low Reynolds number regime (typical Re 10e-3 for fluid velocity 100 microns/sec and length scale 10 microns). However, large particles do not follow the fluid; instead, they are displaced off posts by steric repulsion so even though the fluid may reverse direction, the trajectory of particles which interact with the posts will not necessarily be reversible unless their interaction with the posts is symmetric with the direction of the fluid. In the schematic in FIG. 3A, particles moving to the left are displaced downward by the top row of posts while particles moving to the right are displaced the same amount by the bottom row of posts. However, if we rotate the image 180 degrees, which is analogous to switching the direction of the fluid, the situation is exactly switched, so the result must be the same in either direction. This rotation works because both the lattice points and post shape are invariant under 180 degree rotation. As a result, both large and small particles in bump array with a circular posts will retrace their steps if the flow is switched back and forth.

Numerical simulations showed that the velocity profile through a gap between triangular posts was shifted towards the side of the gap with the vertex. The fluid velocity profile through a gap between posts depends strongly on the local geometry at the gap. For the case of the triangular posts presented here, where there is a sharp vertex on the bottom and a flat edge on the top, a significant deviation from the parabolic flow profile used to describe pressure-driven flow through circular posts should be expected. FIG. 4A shows a numerical simulation of the fluid velocity in an array like that used to produce the particle trajectories in FIG. 2, along with a cross section of the velocity profile across the gap. The line was placed across the smallest spacing between posts to corresponds with the narrowest stream widths where crossing stall lines is most likely to occur. The vertices of the triangle were rounded off with a curvature of 500 nm to approximate the rounding off of a sharp point that results from optical lithography. It was found that the flow profile was invariant under changes in the array tilt so this flow profile can be assumed to be the general flow profile for triangular posts arranged in this way.

FIG. 4B shows a comparison between the flow profiles of triangular and circular posts. For round posts, the profile is nearly parabolic as expected for Poiseuille flow through an infinitely long one-dimensional channel. For triangular posts, however, the flow profile is biased towards the sharp triangular corner pointing up into the flow stream. In other words, the streams bunch closer together near this vertex and the critical particle size for a particle to be bumped across a stall line is smaller than it would be for an array with the same gap size but with round obstacles. Along the flat edge, the opposite is true. Because the fluid travels preferentially along the vertex, the width of the stream along the flat edge is wider than for circular posts. The effect of the triangular posts is to create two separate critical particle sizes, one for moving along the vertex of the triangle and another for moving along the flat edge. Therefore, particles in between these two critical particle sizes should exhibit different behavior depending on which direction they are moving through the array. To show this, we employed the technique used by Inglis et al., 2006, Lab Chip 6:655-658 to estimate the critical particle size for circular posts by using the extracted velocity profile instead of the parabola assumed for circular posts.

Figure 5:
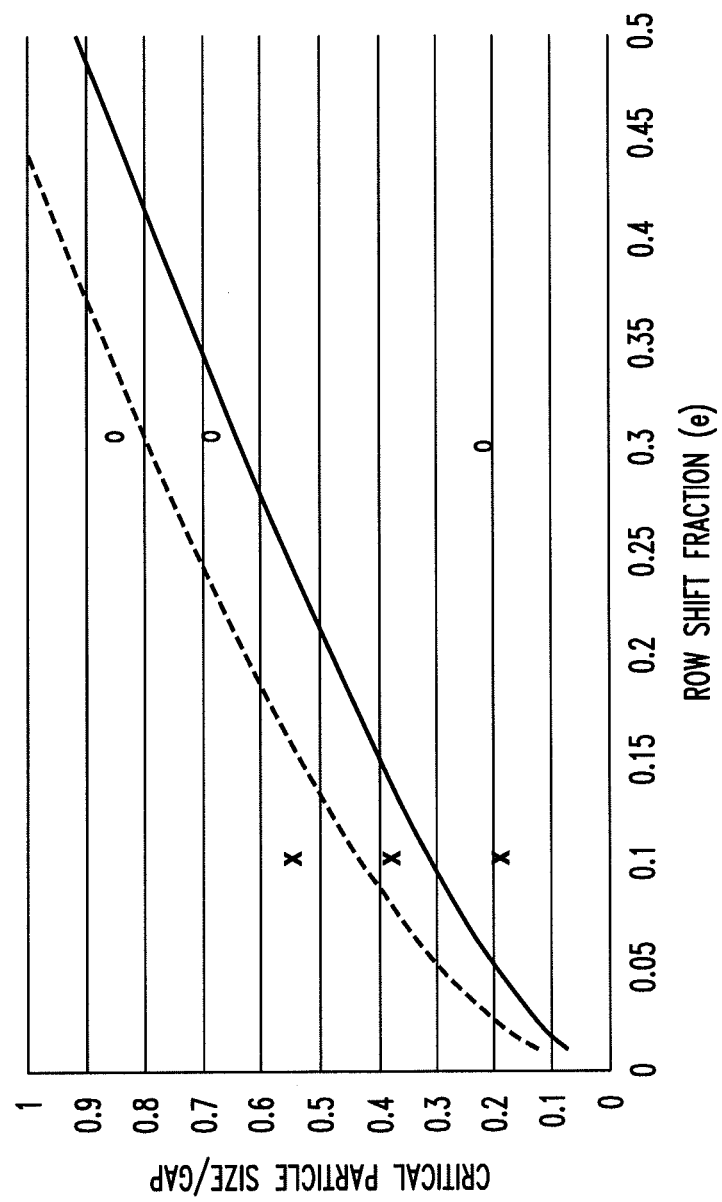

FIG. 5 shows this calculation of the critical particle size as a ratio of the gap for the vertex and flat of the triangle as well as for circular posts versus array tilt angle. The particles shown in figure two are shown as circles on the plot. They show good agreement with the predicted behavior. The 1.1 micron bead is smaller than both critical particle sizes so it travels with the fluid in both directions and shows no net displacement when the fluid direction is cycled. The 3.1 micron particle is bigger than both critical particle sizes so it is displaced along the array axis in both directions and shows no net displacement when the fluid direction is cycled. The 1.9 micron particle is in between the two critical particle sizes so it travels with the fluid when it moves along the flat edge of the triangle and with the array axis when it moves along the vertex of the triangle. As a result, it shows a net displacement when the fluid flow is cycled. This is characteristic of a ratcheting behavior. With no net displacement of the fluid, particles in the intermediate range of an array show a net displacement after several fluid flow oscillations. This ratchet differs from other ratchets in that the ratcheting motion does not occur along the axis of the applied force corresponding to fluid flow in either direction. Rather, it is perpendicular to the motion of the fluid.

Example 2

Bump Array Employing Triangular Posts

This example describes microfluidic arrays which sort particles based on size according to the deterministic lateral displacement method, by using triangular posts instead of the usual round posts. When triangular posts are used rather than round posts, and the triangular posts are properly oriented (i.e., such that the surfaces defining the gap are asymmetric), the critical size is decreased for a given gap size between the posts. This is because the different post geometry on either side of the gap causes an asymmetric flow profile through the gap, with flux shifting towards the vertex of the triangle. This shift in fluid flux reduces the width of the stream that determines the critical particle size. In this example, both experiment and modeling are used to show that changing the post shape from circular to triangular results in several practical advantages over similar arrays with circular posts including increased dynamic range and throughput.

Figure 6A:
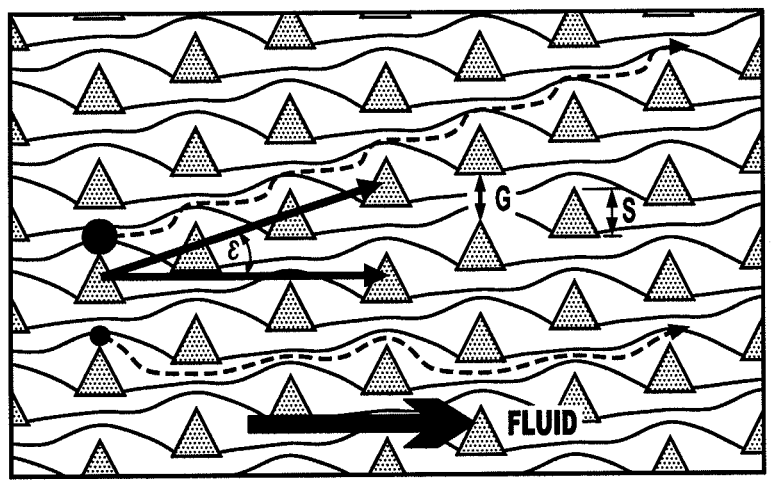

Deterministic lateral displacement is a size-based particle separation technique that relies on selective displacement of particles by an array of obstacles disposed in a flowing fluid. FIG. 6A illustrates a schematic of the relevant array parameters and important features of the devices described in this example. The obstacle array is composed of columns of posts in which each adjacent column is offset a small distance with respect to larger channel walls that dictate the direction of bulk fluid flow ("FLUID" in FIG. 6A). In this case, the posts are equilateral triangles with side length S (contrary to FIG. 6A, S is the side length, not the distance from a vertex of the triangle to the base opposite that vertex). This offset produces an array where an axis along which the obstacles are situated is situated at a tilt angle $\epsilon$ with respect to the direction of fluid flow. The tilt angle is selected such that the array is periodic after $1/\epsilon$ rows. In this case, the fluid flowing through gaps between posts (length of gap is designated G in FIG. 6A) can be partitioned into an integer number of stream tubes delineated by stagnation streamlines. Constrained by the periodicity and the direction of average fluid flow, each of these stream tubes carries an equal volumetric flux.

Particles suspended in the fluid exhibit one of two behaviors depending on their size relative to the width of stream tube nearest to the post as they move through a gap.

Unperturbed by other effects, particles will roughly follow the stream tubes in the fluid flow. This behavior is observed for particles having radii narrower than the stream tube width. These particles, shown as the lower particle and dotted trajectory in FIG. 6A, are not affected by the posts and weave through the array while remain within the bounds of a single stream. As a result, they travel on average in the same direction as the bulk fluid flow. Particles having radii larger than the stream tube width, denoted as the upper particle and dotted trajectory in FIG. 6A, do not fit within a single stream tube as they travel through the gap. Those larger particles are deterministically displaced by the post across the stagnation streamline into the adjacent stream tube. Because of the way the stream tubes cycle through their position in the gap, this displacement will occur at every column of posts and the larger particle will travel along the array axis (i.e., in the array direction, which differs from the bulk fluid direction by the tilt angle $\epsilon$). This binary behavior leads us to describe a critical size which separates these two behaviors. As the particles to be separated are most frequently described by their diameter, we denote the critical size as twice the width of the stream tube nearest to the post in the gap between posts.

Figure 6B:
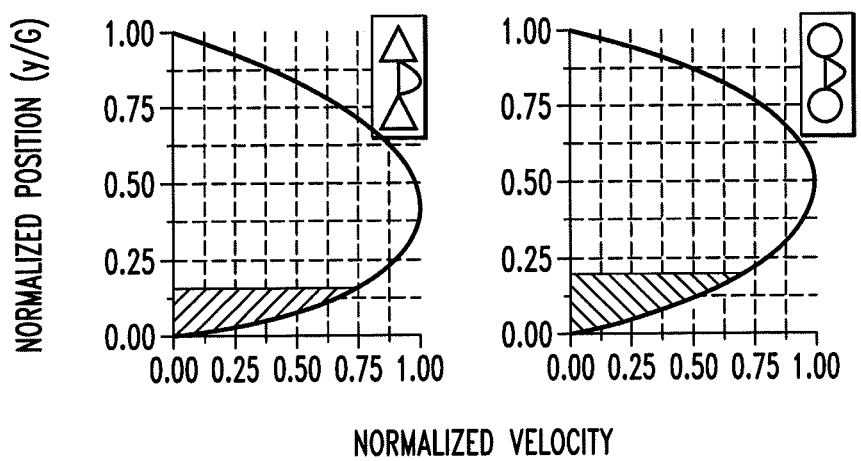

Changing the post shape can have a strong effect on the critical particle size by changing the shape of the flow profile through the gap. Alterations to the flow profile alter the width of the stream tubes nearest the posts that define a gap. Because critical particle size is directly related to these widths, alteration to the flow profile within a gap also alters the critical size(s) defined by the gap. By changing the cross-sectional shape of the posts from the typical circular shape to equilateral triangles, an asymmetry is created in the flow profile through the gap that shifts more fluid flux towards the triangle vertex, as shown in FIG. 6B. This results in different stream tube widths at the top (adjacent the flat edge of a triangular post) and bottom (adjacent the vertex of a triangular post) of the gap and gives the array two distinct critical particle sizes.

The shift in flux towards the vertex of the triangle leads to a reduced stream tube width along this edge and hence reduces the critical particle size corresponding to that stream tube and edge, relative to a similar array with circular posts. This is demonstrated in the two panels of FIG. 6B, which shows numerically simulated flow profiles across the gaps. The two flow profiles, normalized to the width of the gap between posts and the maximum velocity, are plotted side by side for comparison. The fluid constituting the first stream tube for tilt angle $\epsilon=\frac{1}{10}$ has been shaded to emphasize the difference in stream width, decreasing from about 20% of the gap bounded by circular posts to about 15% of the gap bounded by triangular posts. This shift is central to the reduction in critical particle size behavior exhibited by devices with triangular posts. The shifted flow profile created by triangular posts can be used to create a deterministic microfluidic ratchet, as discussed in Example 1. In the information discussed in this example, the focus is on improvement to continuous flow particle separation devices and the deterministic lateral displacement of particles within them that are enabled by changing the post shape.

Figure 7:
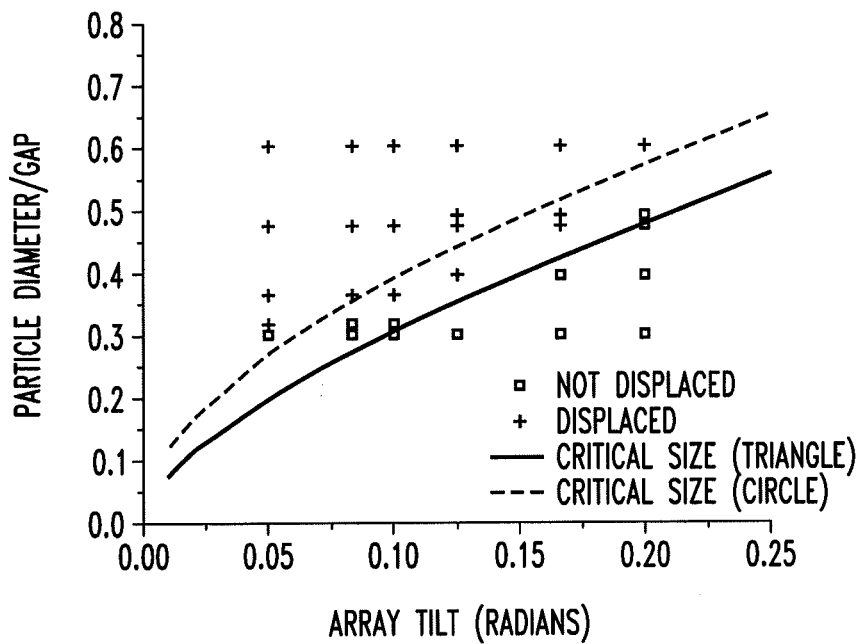
FIG. 7 is a graph illustrating hypothetical and experimental effects of the tilt angle ("Array Tilt" in FIG. 7) on particle displacement.

The reduction in critical particle size enabled by triangular posts was characterized by examining the behavior of fluorescent beads of in arrays with various amounts of array tilt and comparing the results to theoretically predictions. FIG. 7 shows observed particle behavior (displaced by the array or not displaced by the array) normalized to the gap size versus array tilt as well as predicted critical particle sizes using the method described by Inglis et al., 2006, Lab Chip 6:655-658. The lines in FIG. 7 represent the predicted critical particle size for a given tilt angle the solid line representing predictions for arrays with triangular posts and the dotted line representing predictions for arrays with round posts. Particles above the line are expected to be displaced by the array particles below the line are not expected to be displaced. The data demonstrated that there is reasonable agreement with the predicted behavior for higher tilt angles while there is some deviation at the shallower tilt angles, especially at a tilt angle $\epsilon$ of $\frac{1}{20}$ radians. This deviation could be caused by the flow through the array not being completely horizontal, which will have a large affect at shallower array tilts, or because of rounding of the triangular post edges, which will be discussed later in this example.

The predicted particle behavior for circular posts, signified by the dotted line, has been added as a comparison. For any practical tilt angle (between $\frac{1}{5}$ and $\frac{1}{100}$), the critical size in an array with triangular posts is substantially smaller than the critical size in a similar array with circular posts, the difference amounting to up to 10% of the gap for the steeper tilt angles. These properties allow smaller particles to be separated by an array of triangular posts than can be separated by an array of round posts having the same gap spacing. These properties also mean that the gap spacing for triangular posts that is necessary to separate particles of a selected size is larger than the corresponding gap spacing for round posts that would be necessary to separate the same particles.

Figure 8:
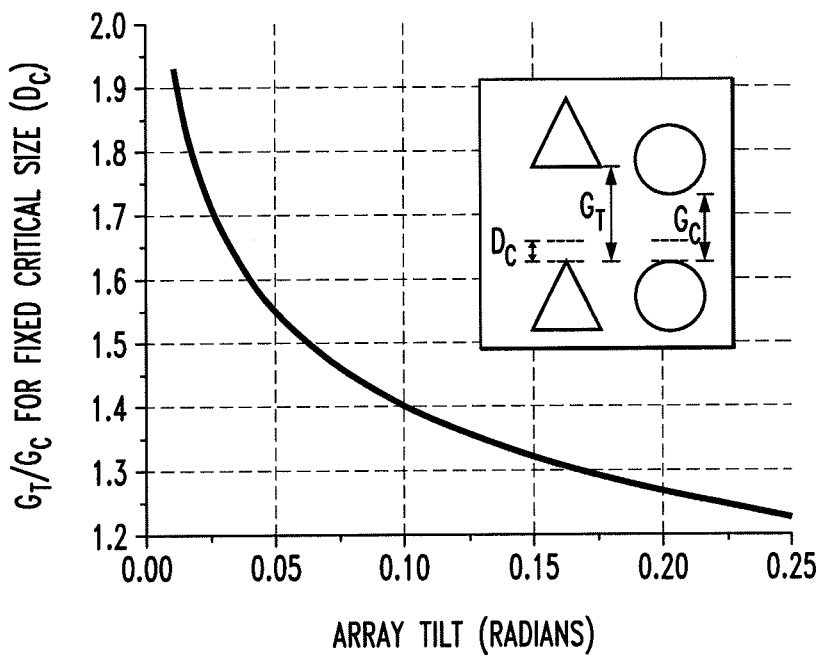
FIG. 8 is a graph illustrating the effect of the tilt angle ("Array Tilt" in FIG. 8) on gap length G. $G_T$ refers to the gap length between triangular posts, and $G_C$ refers to the gap length between round posts.

In either case, a reduced critical particle size as a fraction of the gap is useful in reducing clogging in the array. One of the major limitations of these arrays is that particles larger than the gap will clog the entrance, causing loss of function. Biological samples often contain species with a broad range of sizes so careful filtering or multiple separation stages are necessary to ensure that the array continues to function. Using triangular posts allows one to increase the size of the gap for a given critical particle size and reduce the chances that the array will clog. FIG. 8 illustrates how much larger the gap between posts can be made as a function of the array tilt. Plotted as a ratio of the two gaps for a fixed critical particle size, a minimum 20% improvement can be seen with increasing gap size as the tilt is reduced, with a ratio of 1.25 for a tilt angle of $\frac{1}{4}$ and a ratio of 1.94 for a tilt angle of $\frac{1}{100}$. Thus, shallower tilt angles facilitate use of larger gaps at the cost of a smaller separation angle and increased array size. However, larger gaps provide another benefit in terms of increased array throughput.

A throughput comparison between an array with triangular and circular posts showed a substantial increase in average velocity for a given pressure drop in the array with triangular posts. Arrays with triangular posts or with circular posts were constructed with nearly identical characteristics. They each had the same overall channel width and length, depth, tilt angle ($\frac{1}{10}$), and post size (the diameters of round posts were equal to the side lengths of the equilateral triangular posts). The single variation was the gap between posts, which was designed and verified with numerical simulation to give a critical particle diameter of approximately 3.2 microns for both arrays. Those numerical simulations indicated that the critical particle diameter was achieved using a gap of 10.5 microns in arrays with triangular posts and a gap of 8.3 microns in arrays with circular posts.

The trajectories of 500 nanometer fluorescent beads were recorded with an electron multiplying charged coupled device (EMCCD) camera capturing video at 10 frames per second and then analyzed using MATLAB™ software for a given pressure gradient across the array. Small particles that would not be displaced (i.e., bumped) by the array were chosen so they would sample each of the flow streams evenly and provide an accurate representation of the overall average fluid velocity.

Figure 9:
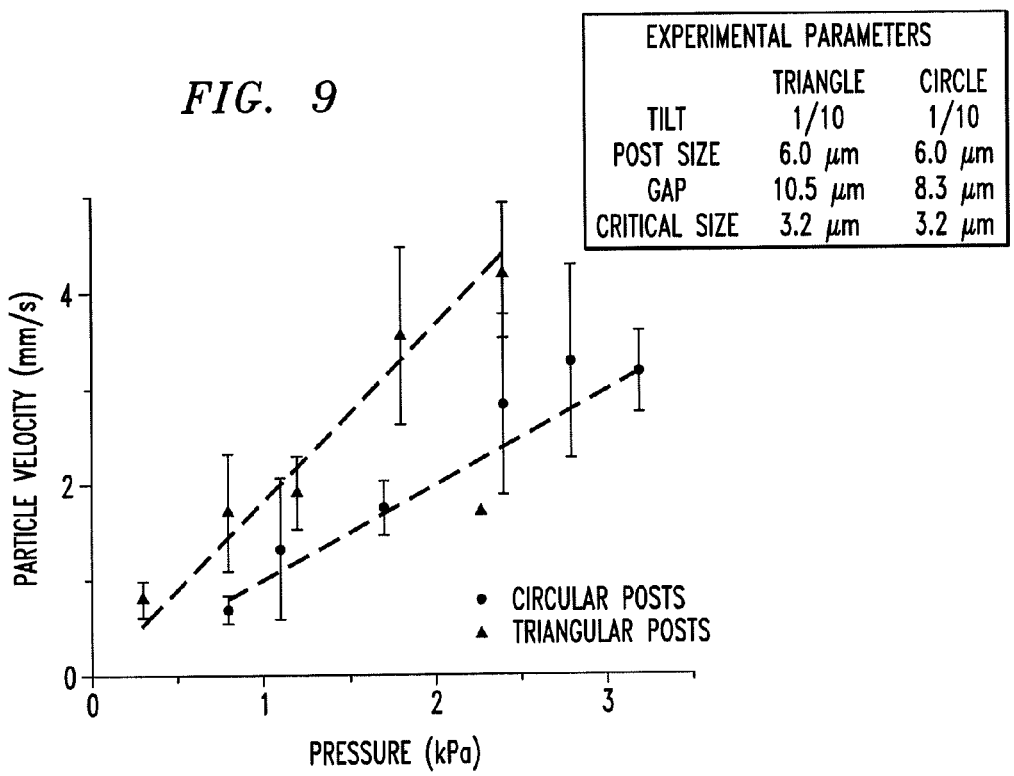
FIG. 9 is a graph illustrating the effect of applied pressure on particle velocity in bump arrays having triangular posts (data shown as triangles) and bump arrays having circular posts (data shown as circles).

The average particle velocities are plotted in FIG. 9 as a function of pressure gradient along with a weighted linear fit. The fitted lines demonstrate that particles in the triangular post array moved much faster. The upper range of pressures was limited by the field of view of the microscope and the capture speed of the camera. Beyond several kPa in pressure, the particles traversed the entire field of view within one or two frames of the video and no accurate estimate of velocity could be made. However, since the Reynolds number in these experiments is on the order of $10^{-2}$, the linear fit can safely be extended into the tens of kPa range to match the expected linear relationship between velocity and pressure that is seen for low Reynolds number flows. The posts need not be triangular in cross-section. Posts having other (square, oblong, or irregular) cross-sectional profiles can also be used, so long as the shape of the obstacles causes the gap to be asymmetric.

Comparing the slopes of the two linear fits in FIG. 9, it can be seen that particles in the array with triangular posts traveled 85% faster on average than those in an array with circular posts. This result agrees with numerical simulation performed with COMSOL™ software that showed that the average velocity for was 82% faster for triangular posts. The mechanism behind these findings can be understood by drawing an analogy to Poiseuille flow between two parallel plates, where the average velocity for a fixed pressure gradient is proportional to the smallest distance between the plates squared. The analogy is not exact because the confining structure is an array of posts instead of two parallel plates, but underscores the benefits of increasing the width of the gap, where just a few microns yields a substantial increase in throughput.

Figure 10:
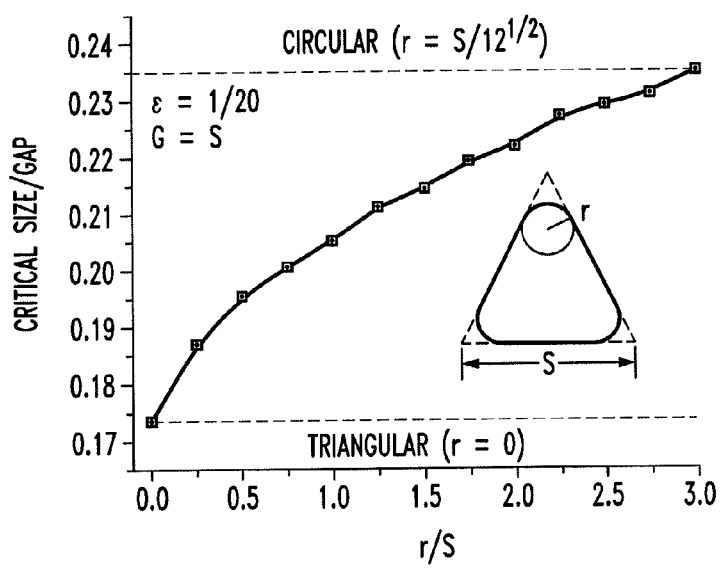
FIG. 10 is a graph illustrating the effect of obstacle edge roundness (expressed as r/S) on the critical size exhibited on the side of a gap bounded by the edge.

The gains achieved by changing the post shape are degraded if care is not taken to maintain sharp post vertices. FIG. 10 shows the effect of rounding triangular post edges on the critical particle size. An array with 10 micron posts, 10 micron gaps between posts, and tilt angle of $\frac{1}{20}$ was simulated using COMSOL™ software, with the vertices rounded to various radii of curvature ranging from none (r=0) to complete rounding where the final shape is a circle ($r=S/12^{1/2}$). Flow profiles across the gaps were extracted for each rounding and the critical size for the given tilt was calculated using previously stated methods. As shown in FIG. 10, there is a dramatic increase in the critical particle size as the post shape transitions from triangular to circular. Starting at 0.174 G when the post is completely triangular (i.e., r=0), critical particle size increases 35% to 0.235 G when the post is completely circular ($r=S/12^{1/2}$). The transition suggests that if a fabrication process that produces an undesirable vertex rounding, sing larger posts (increasing S) will help to maintain the decreased critical particle size that results from using triangular posts.

This observation also helps to explain the deviation from expected behavior observed for some of the fluorescent beads in FIG. 7. SEM images of the posts show vertex rounding (r/S) of 0.118±0.006, which corresponds to an increase in the critical particle size from 0.93 microns to 1.12 microns.

The disclosure of every patent, patent application, and publication cited herein is hereby incorporated herein by reference in its entirety.

While the subject matter has been disclosed herein with reference to specific embodiments, it is apparent that other embodiments and variations of this subject matter can be devised by others skilled in the art without departing from the true spirit and scope of the subject matter. The appended claims include all such embodiments and equivalent variations.

What is claimed is:

1. A bump array device for segregating particles by size, the device comprising:
   a body defining a microfluidic flow channel for containing fluid flow in a first direction and an array of obstacles disposed within and extending across the microfluidic flow channel;
   the obstacles being arranged in rows and columns, wherein the rows define an array direction that differs from the first direction by a tilt angle ($\epsilon$);
   the columns repeat periodically and have a periodicity that is equal to $1/\epsilon$, where $\epsilon$ is measured in radians;
   the obstacles in each respective column defining gaps between themselves through which the fluid can flow generally transversely with respect to the columns; and
   the obstacles being shaped such that surfaces of two obstacles defining a respective gap are asymmetrically oriented about a first plane that extends through the center of the respective gap and that is parallel to the first direction.

2. The device of claim 1, wherein the surfaces of each of the two obstacles defining a respective gap are non-parallel, substantially planar surfaces.

3. The device of claim 2, wherein each of the two obstacles defining a respective gap has a triangular cross-section.

4. The device of claim 1, wherein the surface of one of the two obstacles defining a respective gap is curved and the surface of the other obstacle defining the respective gap is substantially planar.

5. The device of claim 1, wherein the microfluidic flow channel is bounded by a pair of parallel, substantially planar surfaces between which the obstacles extend.

6. The device of claim 1, wherein the rows and columns are at an angle of 90 degrees with respect to one another.

7. The device of claim 1, wherein the shape of each of multiple obstacles in a column is substantially identical and symmetrical about a second plane that bisects each of the multiple obstacles.

8. The device of claim 7, wherein the shape of substantially all obstacles in the array is substantially identical.

9. The device of claim 1, further comprising a liquid completely filling the flow channel.

10. The device of claim 9, further comprising a fluid handling apparatus for providing liquid to, withdrawing liquid from, or both providing liquid to and withdrawing liquid from the microfluidic flow channel.

11. The device of claim 1, wherein the surface of at least one of the two obstacles is a planar surface upstream of the gap and has a sharp edge at the gap.

12. A bump array device for segregating particles by size, the device comprising:
   a body defining a microfluidic flow channel for containing fluid flow in a first direction and a second direction;
   an array of obstacles disposed within and extending across the microfluidic flow channel;
   the obstacles being arranged in rows and columns, wherein the rows define an array direction that differs from the first direction by a tilt angle ($\epsilon$);
   the columns repeat periodically and have a periodicity that is equal to $1/\epsilon$, where $\epsilon$ is measured in radians;
   the obstacles in each respective column defining gaps between themselves through which the fluid can flow in the first direction generally transversely with respect to the columns and through which the fluid can flow in the second direction generally transversely with respect to the column; and
   the obstacles being shaped such that the critical particle size for particles passing through each gap in the first direction is different than the critical particle size for particles passing through each of the gaps in the second direction.

13. The device of claim 12, wherein the first and second directions are offset at an angle of from 120 to 180 degrees.

14. The device of claim 12, wherein the first and second directions are offset by 180 degrees.

15. The device of claim 12, wherein the obstacles extend between essentially parallel faces of the microfluidic flow channel.

16. The device of claim 12, wherein the transverse cross-section of each of the two obstacles defining a respective gap is substantially triangular.

17. A method of segregating particles, the method comprising:
   inducing movement of a fluid in a first direction in a flow channel having a multiplicity of obstacles disposed therein and extending thereacross;
   the fluid having the particles suspended therein;
   the obstacles being arranged in rows and columns, wherein the rows define an array direction that differs from the first direction by a tilt angle ($\epsilon$);
   the columns repeat periodically and have a periodicity that is equal to $1/\epsilon$, where $\epsilon$ is measured in radians;
   the obstacles in each respective column defining gaps between themselves through which the fluid can flow generally transversely with respect to the columns;
   the obstacles being shaped such that the surfaces of two obstacles defining a respective gap are asymmetrically oriented about a first plane that extends through the center of the gap and that is parallel to the first direction; and
   whereby the velocity profile of fluid flow through the gap is asymmetrically oriented about the first plane and the critical particle size for particles passing through each respective gap adjacent to one of the two obstacles is different than the critical particle size for particles passing through each respective gap adjacent to the other of the two obstacles.

18. A method of segregating particles, the method comprising:
    inducing discrete, alternate movement of a fluid in a first direction and a second direction, in a flow channel having a multiplicity of obstacles disposed therein and extending thereacross;
    the fluid having the particles suspended therein;
    the obstacles being arranged in rows and columns, wherein the rows define an array direction that differs from the first direction by a tilt angle ($\epsilon$);
    the columns repeat periodically and have a periodicity that is equal to $1/\epsilon$, where $\epsilon$ is measured in radians;
    the obstacles in each respective column defining gaps between themselves through which the fluid can flow in the first direction generally transversely with respect to the columns and through which the fluid can flow in the second direction generally transversely with respect to the columns;
    the obstacles being shaped such that the critical particle size for particles passing through each gap in the first direction is different than the critical particle size for particles passing through each gap in the second direction; and
    whereby particles intermediate in size between i) the critical particle size for particles passing through each gap in the first direction and ii) the critical particle size for particles passing through each gap in the second direction are separated from other particles.

19. A bump array device comprising
    a body defining a microfluidic flow channel for containing fluid flow in a first direction;
    an array of obstacles within and extending across the microfluidic flow channel and arranged in rows and columns, wherein the rows define an array direction that differs from the first direction by a tilt angle ($\epsilon$);
    the columns repeat periodically and have a periodicity that is equal to $1/\epsilon$, where $\epsilon$ is measured in radians;
    the obstacles in each set of two proximal obstacles in a respective one of the columns are separated by a respective gap through which the fluid can flow generally transversely with respect to the columns; and
    the obstacles being shaped such that the surfaces of the two proximal obstacles defining each of the respective gaps are asymmetrically oriented about a plane that extends through the center of each of the respective gaps and is parallel to the first direction.

20. A method of segregating particles, the method comprising:
    inducing movement of a fluid in a flow channel either in a first direction or alternating between the first direction and a second direction;
    the fluid having the particles suspended therein;
    the flow channel having a multiplicity of obstacles disposed therein and extending thereacross, the obstacles being arranged in rows and columns, wherein the rows define an array direction that differs from the first direction by a tilt angle ($\epsilon$);
    the columns repeat periodically and have a periodicity that is equal to $1/\epsilon$, where $\epsilon$ is measured in radians;
    the obstacles in each set of two proximal obstacles in a respective one of the columns separated by a respective gap and through which the fluid can flow generally transversely with respect to the columns; and
    the obstacles being shaped such that the surfaces of obstacles in each set of two proximal obstacles separated by a respective gap are asymmetrically oriented about a plane that extends through the center of the respective gap.

* * * * *